US005935399A

United States Patent [19]
Tanaka et al.

[11] Patent Number: 5,935,399
[45] Date of Patent: Aug. 10, 1999

[54] AIR-FUEL RATIO SENSOR

[75] Inventors: Akio Tanaka, Oobu; Naoto Miwa, Tsushima; Hiromi Sano, Nagoya; Toshitaka Saito, Toyohashi; Katsuhiro Ishikawa, Nisshin, all of Japan

[73] Assignee: Denso Corporation, Kariya, Japan

[21] Appl. No.: 08/792,737

[22] Filed: Jan. 31, 1997

[30] Foreign Application Priority Data

Jan. 31, 1996 [JP] Japan ..................................... 8-039011
Mar. 15, 1996 [JP] Japan ..................................... 8-087368

[51] Int. Cl.[6] ................................................ G01N 27/407
[52] U.S. Cl. ........................ 204/424; 204/425; 204/427; 204/428; 204/429
[58] Field of Search ..................................... 204/421–429

[56] References Cited

U.S. PATENT DOCUMENTS

| 4,076,608 | 2/1978  | Fujishiro et al. | 204/427 |
| 4,177,112 | 12/1979 | Suzuki et al.    | 204/429 |
| 4,383,906 | 5/1983  | Sano et al.      | 204/429 |
| 4,402,820 | 9/1983  | Sano et al.      | 204/429 |
| 4,502,939 | 3/1985  | Holfelder et al. | 204/425 |
| 4,541,898 | 9/1985  | Mase et al.      | 204/425 |
| 4,541,900 | 9/1985  | Mase et al.      | 204/425 |
| 4,578,174 | 3/1986  | Kato et al.      | 204/427 |
| 4,636,293 | 1/1987  | Bayha et al.     | 204/427 |

FOREIGN PATENT DOCUMENTS

| 58-076757 | 5/1983 | Japan . |
| 59-095257 | 6/1984 | Japan . |
| 6013488   | 4/1994 | Japan . |

Primary Examiner—T. Tung
Attorney, Agent, or Firm—Pillsbury Madison & Sutro LLP

[57] ABSTRACT

An air-fuel ratio sensing element comprises a cup-shaped solid electrolyte with one end opened and the other end closed, an external electrode provided on an outer wall surface of the solid electrolyte so as to be exposed to measured gas, and an internal electrode provided on an inner wall surface of the solid electrolyte in a confronting relationship to the external electrode. A first insulating layer, made of a gas-permeable and nonconductive porous material, is provided on the external electrode at least in a region used for detecting of an air-fuel ratio. A second insulating layer is provided outside the first insulating layer and, a heater layer as provided between the first insulating layer and the second insulating layer.

30 Claims, 24 Drawing Sheets

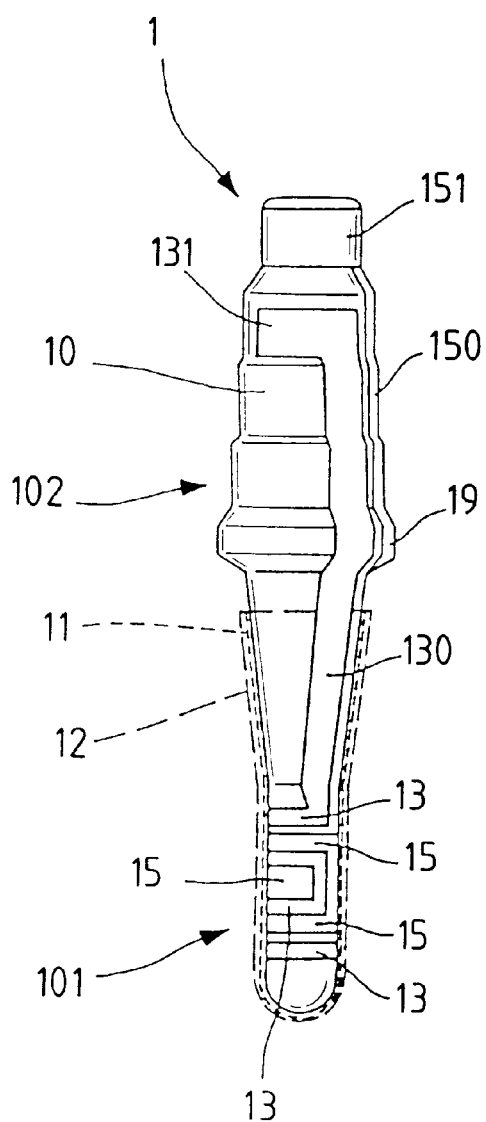
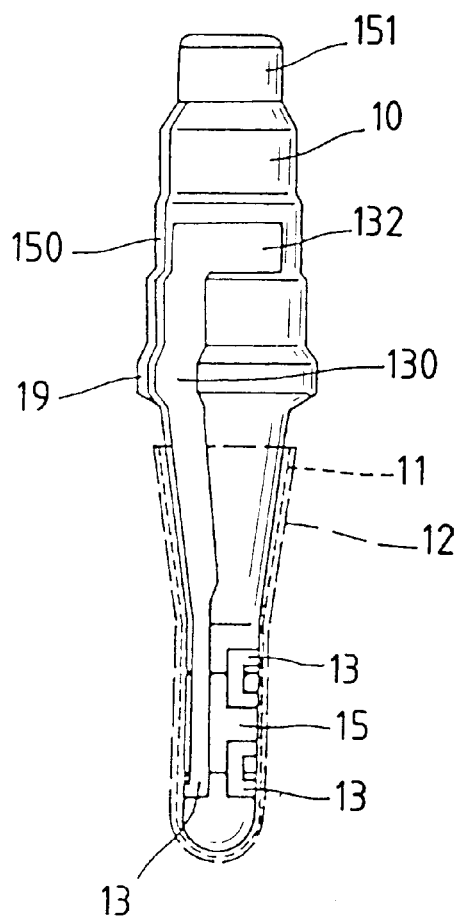

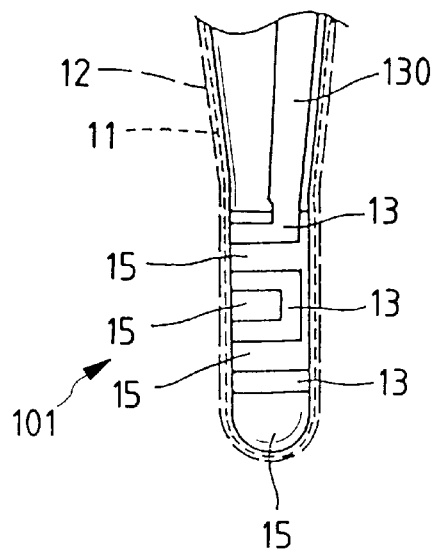
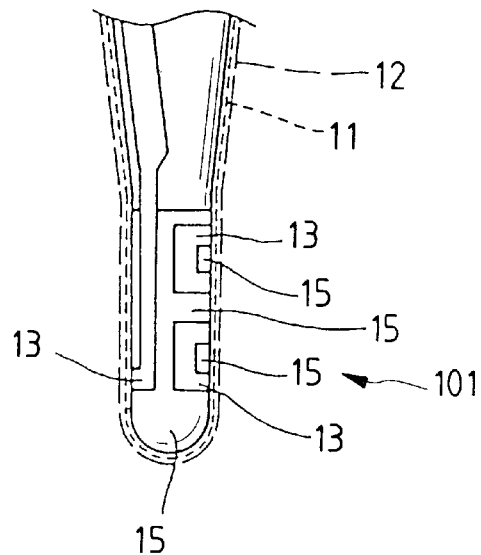
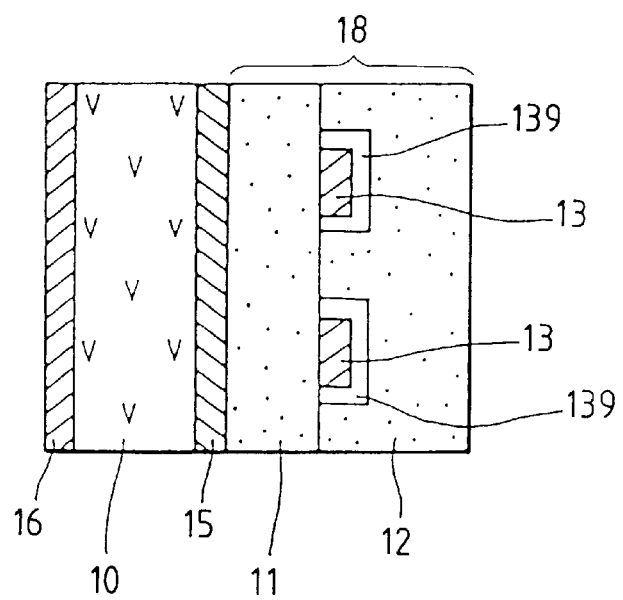

FIG. 28A
FIG. 28B
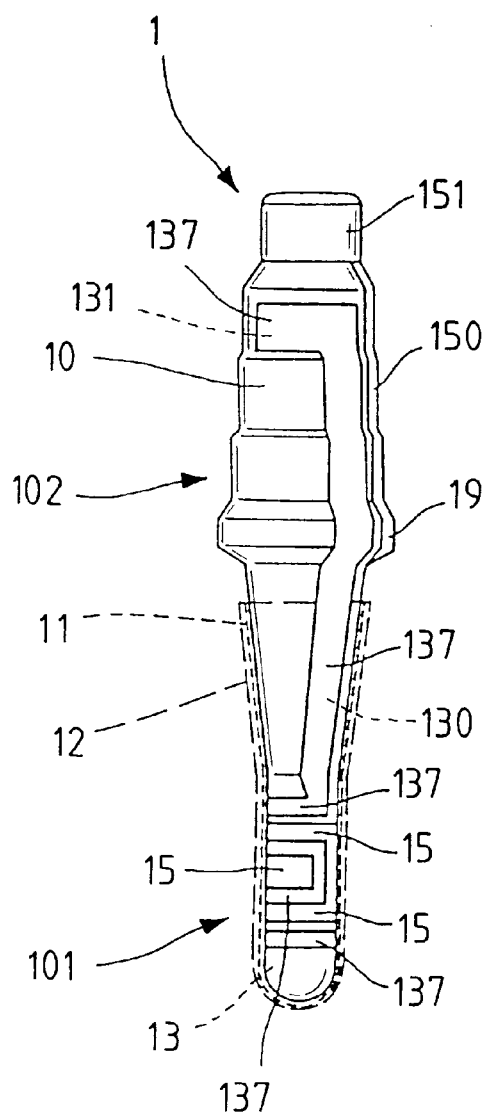
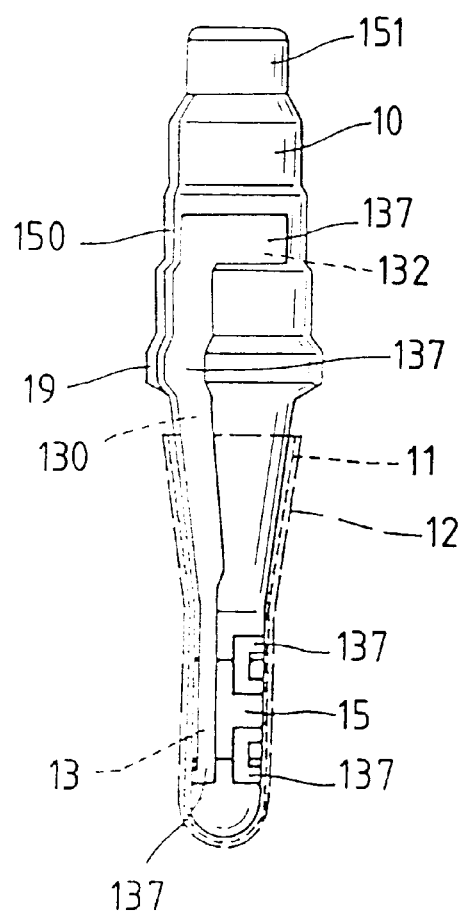

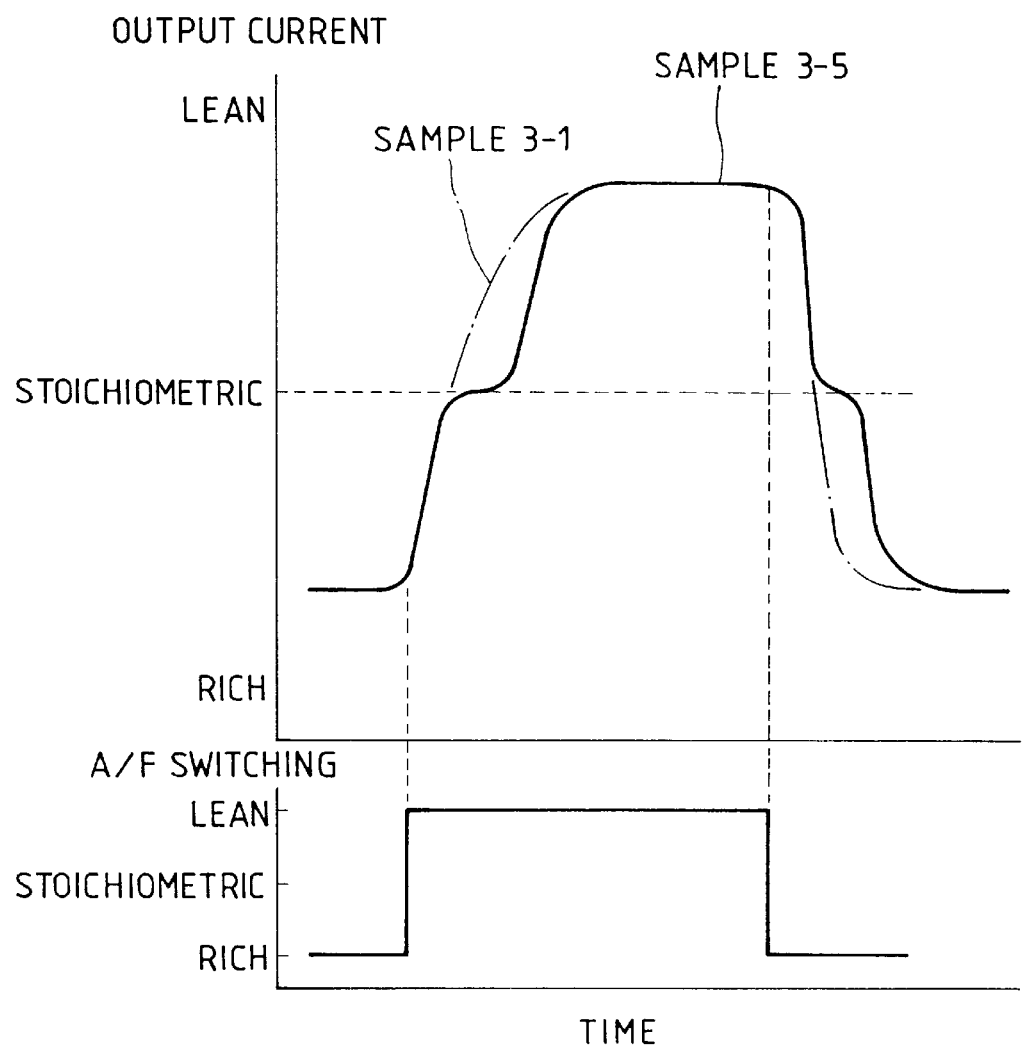

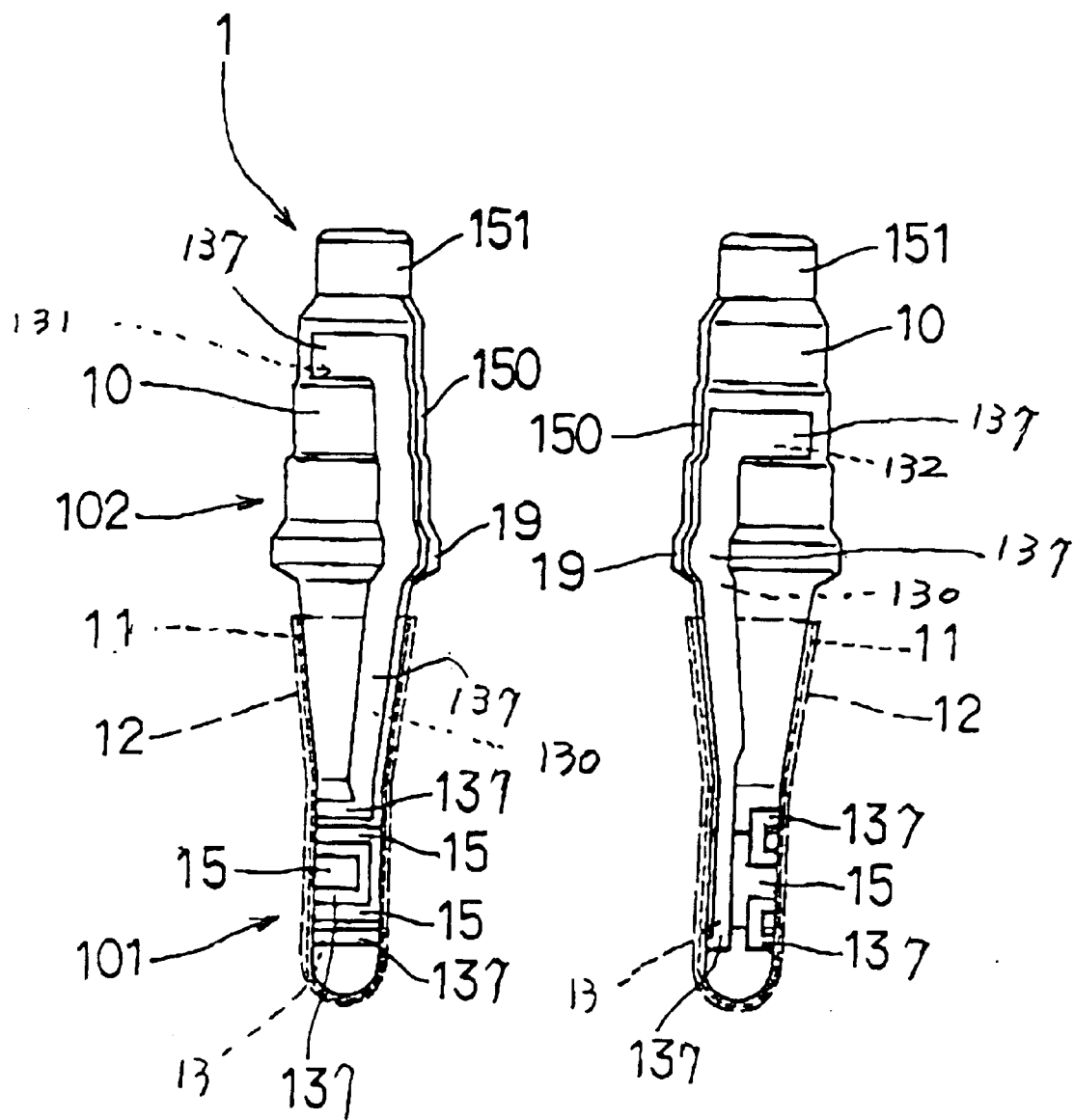

FIG. 32A    FIG. 32B
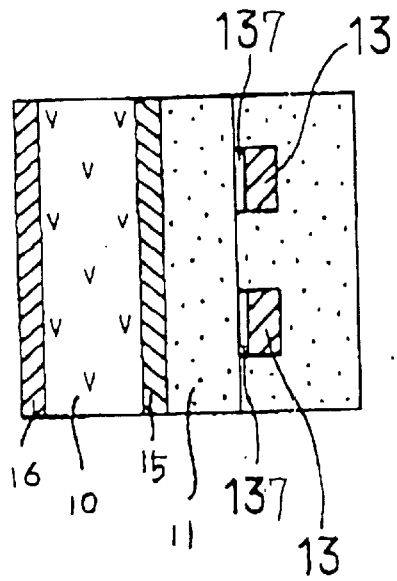
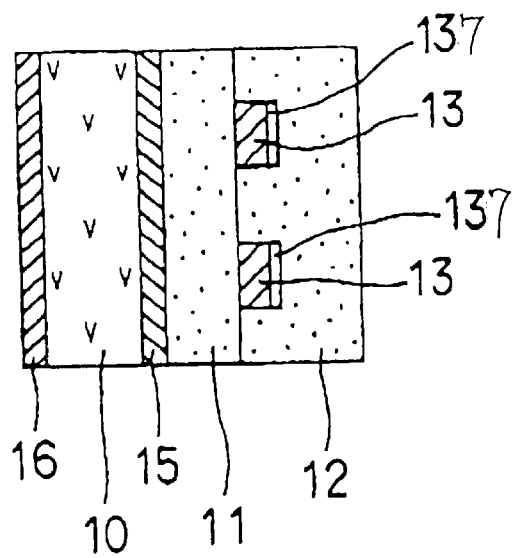
FIG. 33
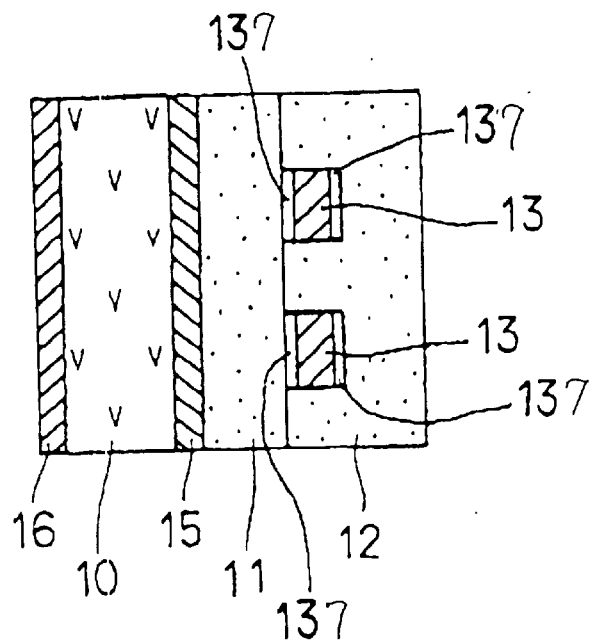

AIR-FUEL RATIO SENSOR

BACKGROUND OF THE INVENTION

1. Field of the Invention

This invention relates to an air-fuel ratio (e.g., oxygen concentration) sensor provided in an exhaust gas system for an internal combustion engine of an automotive vehicle.

2. Description of Related Art

Gas concentration detectors are incorporated in many of recent internal combustion engines for automotive vehicles to detect and feedback control the air-fuel ratio of the gas mixture introduced into their combustion chambers. The air-fuel ratio by a gas concentration detector is generally used to control the combustion of air/fuel mixture in the combustion chamber to emit exhaust gas suitable for a attaining an optimum gas purification efficiency in the exhaust gas system comprising a catalytic converter.

An ordinary oxygen concentration detector comprises an oxygen concentration sensing element with a $ZrO_2$ solid electrolyte and a housing accommodating this oxygen concentration sensing element. Oxygen concentration sensing elements are roughly classified into listing current type detectors and oxygen concentration cell type detectors.

FIGS. 34 and 35 cooperatively show one example of the oxygen concentration sensing element which has a solid electrolyte of a cup shape, i.e., a cylindrical shape having a bottom.

More specifically, an oxygen concentration sensing element 9 comprises a cup-shaped solid electrolyte 90, an external electrode 95 provided on an outer wall surface of solid electrolyte 90, an internal electrode 96 provided on an inner wall surface of solid electrolyte 90, and an insulating layer 91 provided on the surface of external electrode 95.

Furthermore, oxygen concentration sensing element 9 has an inside hollow space defining an inside chamber 92 for introducing a reference gas. A round stick-like heater 99 is inserted into this inside chamber 92 and held therein. Insulating layer 91, capable of serving as a protecting layer for the external electrode 95, is formed by a ceramic coating layer. Insulating layer 91 may be a complex layer comprising, for example, a $\gamma$-$Al_2$ $O_3$ layer formed on the ceramic coating layer.

To clear the regulations for exhaust gas emission which yearly become more severe, it is required to control the air-fuel ratio more precisely to realize an optimum combustion in an automotive vehicle's internal combustion engine. In this respect, developing an accurate oxygen concentration sensing element is a key factor to realize such an excellent air-fuel ratio control.

For example, among such advanced oxygen concentration sensing elements, there is an oxygen concentration sensing element capable of quickly warming up to detect an oxygen concentration within a short period of time from a start-up operation of the automotive vehicle's internal combustion engine.

In general, every oxygen concentration sensing element has an element active temperature. At or above this element active temperature, the oxygen concentration sensing element can operate normally. Immediately after the internal combustion engine is started, temperatures of the exhaust system and its peripheral components are relatively low. Accordingly, the heater inserted in the inside chamber is actuated to increase the temperature of the oxygen concentration sensing element promptly to its element active temperature. This is why the heater is necessary to warm up the sensing element.

In view of the thermal efficiency during a warm-up operation of an oxygen concentration sensing element, it is generally advantageous to provide a heater integrally with the sensing element, rather than providing a separate heater. Such an oxygen concentration sensing element is, for example, disclosed in Unexamined Japanese Patent Application No. SHO 58-76757, published in 1983, wherein an electrically activated heater layer is provided on a wall surface of a solid electrolyte (except a region of an external electrode).

However, according to the oxygen concentration sensing element disclosed in this prior art, there is a problem that the temperature of the solid electrolyte is excessively increased when a higher voltage is applied to the heater layer, because the heater layer is provided directly on the surface of the solid electrolyte. In this case, components constituting the solid electrolyte, such as $ZrO_2$, may be subjected to reduction and decomposition due to the applied electrical potential and heat. This leads to a deterioration in the insulation property between the external electrode and the internal electrode, causing a problem of inaccurate detection of the oxygen concentration. Moreover as, the solid electrolyte is deteriorating, a leak current flows from the heater layer into an oxygen concentration detecting circuit.

The oxygen concentration detection circuit, in this case, is an electric circuit for judging a concentration of oxygen involved in the measured gas based on an output signal (i.e., electric voltage or electric current) generated from the oxygen concentration sensing element. The external electrode and the internal electrode, as well as later-described external electrode lead, internal electrode lead, external electrode terminal and internal electrode terminal, respectively constitute part of the oxygen concentration detection circuit.

Furthermore, according to the oxygen concentration sensing element disclosed in the prior art, a distance between the heater and the external or internal electrode is not short when compared with that of a conventional separate type heater. Hence, its warm-up ability is not satisfactory.

Unexamined Japanese Utility Model Application No. SHO 59-95257, published in 1984, discloses another oxygen concentration sensing element with an integral heater, wherein a coil-like heater is provided on the outer cylindrical surface of the oxygen concentration sensing element.

However, according to this prior art, a relatively large amount of thermal energy is transmitted or radiated to the outside because the heater is provided on the outer cylindrical surface. The percentage of thermal energy actually transferred to the oxygen concentration sensing element is small. Hence, its warm-up ability is not satisfactory.

SUMMARY OF THE INVENTION

Accordingly, in view of above-described problems encountered in the related art, a principal object of the present invention is to provide an air-fuel ratio (oxygen concentration) sensor comprising an air-fuel ratio (i.e.,) sensing element having a reliable durability and excellent detection accuracy as well as an excellent warm-up ability.

In order to accomplish this and other related objects, the present invention provides an air-fuel ratio sensing element comprising a solid electrolyte formed into a cup-shaped configuration with a one end (i.e., top) opened and the other end (i.e., bottom) closed, an external electrode provided on an outer wall surface of the solid electrolyte so as to be exposed to measured gas, and an internal electrode provided on an inner wall surface of the solid electrolyte in a confronting relationship to the external electrode. Furthermore, a first insulating layer is provided on the external electrode at least in a region used for detection of an air-fuel ratio. This first insulating layer is formed by a gas-permeable and electrically nonconductive porous material. A second insulating layer is provided outside the first insulating layer. This second insulating layer is nonconductive. And, a heater layer is provided between the first insulating layer and the second insulating layer.

According to features of preferred embodiments of the present invention, the second insulating layer is formed by a gas-permeable porous material. Or, the second insulating layer is formed by a gas impervious material. The first insulating layer has a thickness of 10–900 μm and a porous rate of 1–50%. The heater layer is formed by an electrically conductive material and hyaline. Alternatively, the heater layer is formed by an electrically conductive material, and the electrically conductive material contains at least one of the noble metallic powder and the perovskite type oxide powder. Alternatively, the heater layer is made of metallic wire or metallic foil.

Furthermore, it is preferable that the air-fuel ratio sensing element of the present invention after comprises a heater lead connected to the heater layer, an external electrode lead connected to the external electrode, and an internal electrode lead connected to the internal electrode. The heater lead, external electrode and internal electrode are provided along the wall surfaces of the solid electrolyte.

The solid electrolyte may have a closed end portion closer to the other end (i.e., bottom) thereof and a barrel portion formed at an intermediate portion. In this case, the heater is provided in a predetermined region of the closed end portion while a heater terminal is provided on the barrel portion, and the heater terminal is connected to the heater layer via a heater lead. The first insulating layer is formed on the outer wall surface of the solid electrolyte so as to extend to a region of the heater terminal.

It is preferable that a flush surface is partly formed on the first insulating layer, and the heater layer is formed on the flush surface. The flush surface has a surface roughness of 0–30 μm.

Furthermore, it is preferable that the heater layer has an oxygen absorbing force weaker than that of the external electrode. The heater layer is made of an alloy comprising platinum and gold, with a mixing rate of the gold in a range of 0.5–50 weight %. The heater layer contains platinum and at least one component selected from the group consisting of Pd, Rh and Ir.

Moreover, the heater lead and the external electrode lead have a catalytic action of oxidation and reduction to the measured gas smaller than that of the external electrode. The heater lead is made of gold. Alternatively, the heater lead is made of an alloy containing gold and at least one component selected from the group consisting of Pt, Pd, Rh and Ir.

Furthermore, the air-fuel sensing element of the present invention is accommodated in a housing to constitute an air-fuel ratio detector. In this case, the air-fuel ratio sensing element can be directly supported by the housing, or indirectly supported by the housing via a metallic washer or an insulator.

It is also preferable that the second insulating layer is formed along the outer surface of the first insulating layer so as to extend to a region where the air-fuel ratio sensing element is supported to the housing.

Another second aspect of the present invention provides an air-fuel ratio sensing element comprising a solid electrolyte formed into a cup-shaped configuration with one end opened and the other end closed, an external electrode provided on an outer wall surface of the solid electrolyte so as to be exposed to measured gas, and an internal electrode provided on an inner wall surface of the solid electrolyte in a confronting relationship to the external electrode. Furthermore, a first insulating layer is provided on the external electrode at least in a region used for detection of an air-fuel ratio. This first insulating layer is formed by a gas-permeable and electrically nonconductive porous material. A nonconductive second insulating layer is provided outside the first insulating layer. A heater layer is provided between the first insulating layer and the second insulating layer. A gas protecting layer is provided on at least an outer surface of the heater layer. This gas protecting layer has a gas permeability smaller than that of the first insulting layer.

It is preferable that the gas protecting layer is coated entirely on the surface of the heater layer. The gas protecting layer is made of a heat-resistive inorganic oxide having a porous rate not larger than 5%. In this case, the heat-resistive inorganic oxide is glass or ceramic. The gas protecting layer has a thickness of 1–100 μm.

BRIEF DESCRIPTION OF THE DRAWINGS

The above and other objects, features and advantages of the present invention will become more apparent from the following detailed description which is to be read in conjunction with the accompanying drawings, in which:

FIG. 1A is a side view showing a right side of an oxygen concentration sensing element in accordance with a first embodiment of the present invention;

FIG. 1B is a side view showing a left side of the oxygen concentration sensing element in accordance with the first embodiment of the present invention;

FIG. 8A is a side view partly showing a right side of another oxygen concentration sensing element in accordance with the first embodiment of the present invention;

FIG. 8B is a side view partly showing a left side of the oxygen concentration sensing element in accordance with the first embodiment of the present invention;

FIG. 9 is a vertical cross-sectional view showing an essential arrangement of the oxygen concentration sensing element in accordance with a third embodiment of the present invention;

FIG. 28A is a side view showing a right side of an oxygen concentration sensing element in accordance with a twelfth embodiment of the present invention;

FIG. 28B is a side view showing a left side of the oxygen concentration sensing element in accordance with the twelfth embodiment of the present invention;

DESCRIPTION OF THE PREFERRED EMBODIMENTS

Figure 2:
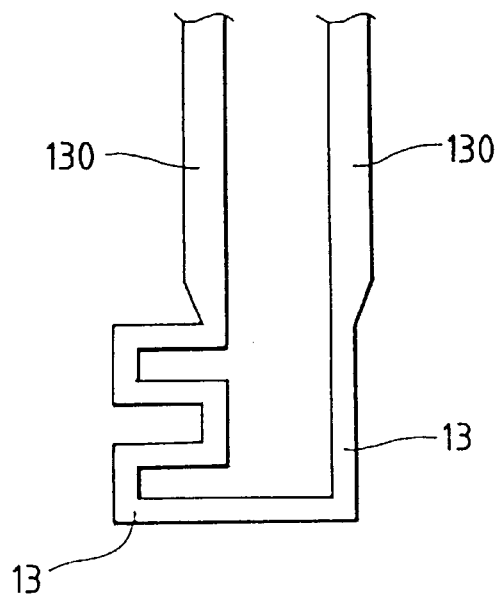
FIG. 2 is a development view showing a heater incorporated in the oxygen concentration sensing element in accordance with the first embodiment of the present invention.

Preferred embodiments of the present invention will be explained hereinafter with reference to accompanied drawings. Identical parts are denoted by the same reference numerals throughout the drawings.

First embodiment

A first embodiment of the present invention will be explained with reference to FIGS. 1A through 8.

As shown in FIGS. 1A through 4, an oxygen concentration detector 2 of the first embodiment comprises an oxygen concentration sensing element 1. The oxygen concentration sensing element 1 comprises a cup-shaped solid electrolyte 10 with one end (i.e., its top) opened and the other end (i.e., its bottom) closed, an external electrode 15 provided on an outer wall surface of this solid electrolyte 10 and exposed to measured gas, and an internal electrode 16 provided on an inner wall surface of the solid electrolyte 10 in a confronting relationship with the external electrode 15 via the solid electrolyte 10. The oxygen concentration sensing element 1 is accommodated in a housing 20.

An insulating layer 18 is provided on a surface of the external electrode 15 at a predetermined region including a specific region used for the detection of oxygen concentration.

Figure 3:
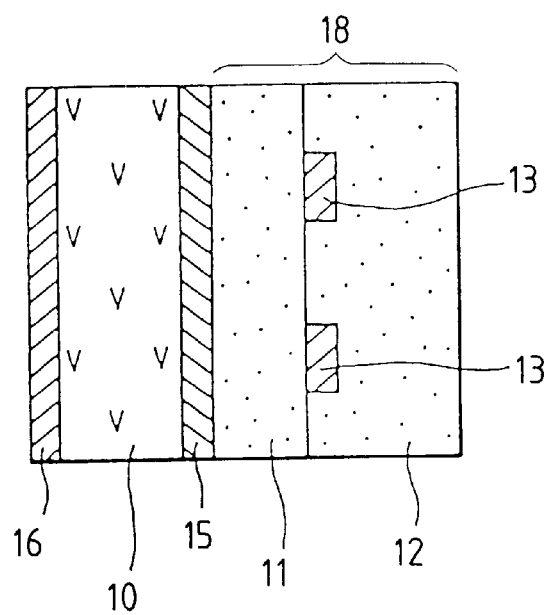
FIG. 3 is a vertical cross-sectional view showing an essential arrangement of the oxygen concentration sensing element in accordance with the first embodiment of the present invention.

As shown in FIG. 3, insulating layer 18 comprises a first insulating layer 11 formed by a gas-permeable and electrically nonconductive porous material, and an electrically nonconductive second insulating layer 12 provided on the outer surface of first insulating layer 11. A heater layer 13 is interposed between first insulating layer 11 and second insulating layer 12. The second insulating layer 12 is also formed by a gas-permeable porous material.

The solid electrolyte 10, as shown in FIGS. 1A and 1B, comprises a closed end portion 101 around which external electrode 15 is wound cylindrically, and a barrel portion 102 having a diameter larger than that of closed end portion 101. A flange portion 19 is provided on a cylindrical outer surface of barrel portion 102 so as to protrude radially outward therefrom at the center thereof.

Solid electrolyte 10 is provided with an external electrode lead 150 and an external electrode terminal 151 which are extended from external electrode 15.

Heater layer 13, as shown in FIG. 3, is provided on the external electrode 15 via first insulating layer 11. There are heater terminals 131 and 132 provided on the surface of solid electrolyte 10, each of heater terminals 131 and 132 extending along the outer wall surface of solid electrolyte 10 and being connected to heater layer 13 via a heater lead 130.

As shown in FIGS. 1A, 1B and 2, each of heater lead 130, heater terminals 131 and 132 has a width thicker than that of heater layer 13. Furthermore, heater terminals 131 and 132 are connected to both ends of a single elongated heater layer 13. A positive voltage is applied through one heater terminal 131 also, while a negative voltage is applied to the other heater terminal 132.

First and second insulating layers 11 and 12 are provided below the flange portion 19 of solid electrolyte 10. This arrangement is suitable for an oxygen concentration detector 2 shown in FIG. 5, wherein an insulator 216 and a washer packing 217 are interposed between oxygen concentration sensing element 1 and housing 20.

Next, the oxygen concentration detector 2 will be explained in greater detail.

Figure 4:
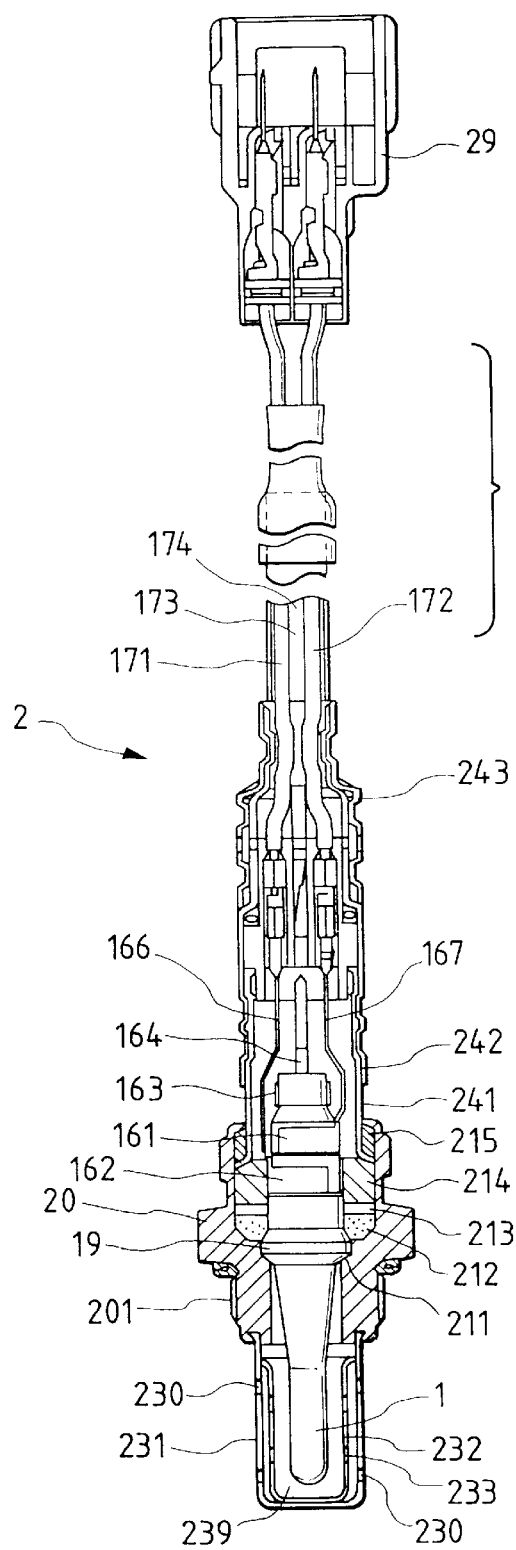
FIG. 4 is a vertical cross-sectional view showing an overall arrangement of an oxygen concentration detector in accordance with the first embodiment of the present invention.
Figure 5:
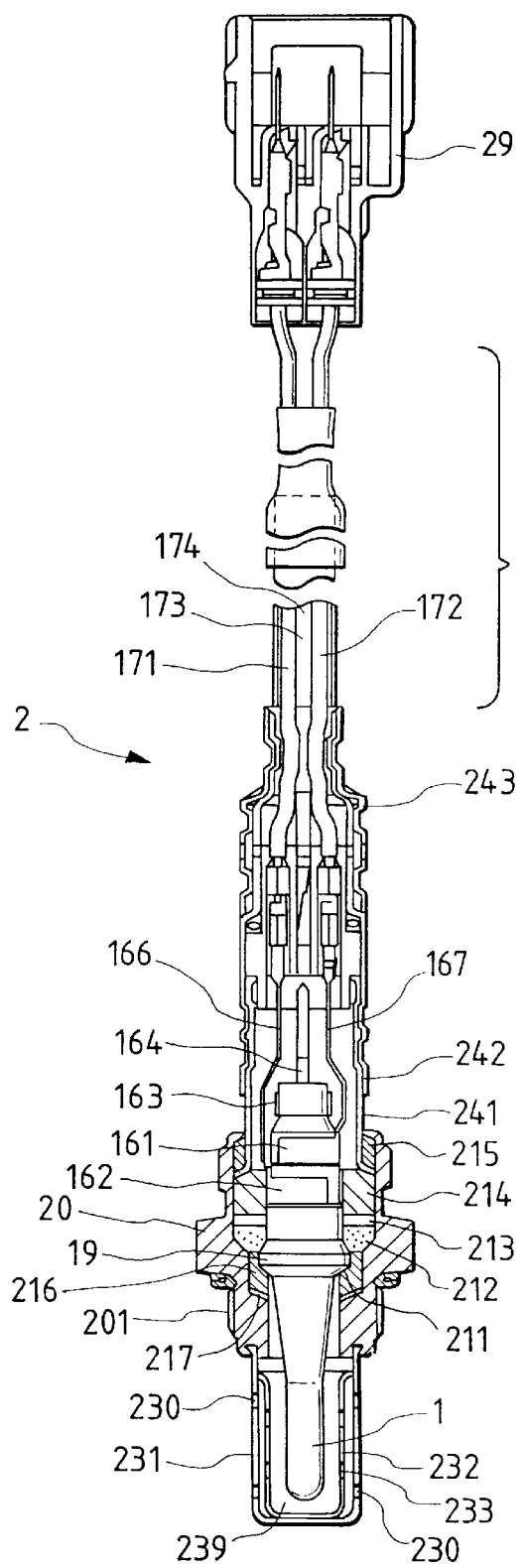
FIG. 5 is a vertical cross-sectional view showing an overall arrangement of another oxygen concentration detector in accordance with the first embodiment of the present invention.

As shown in FIG. 4, oxygen concentration detector 2 comprises a housing 20 for fixedly holding oxygen concentration sensing element 1, double element protectors 231, 232 provided at a lower end of housing 20 to protect oxygen concentration sensing element 1, and atmospheric covers 241, 242 and 243 sequentially provided at an upper end of housing 20. Element protectors 231 and 232 cooperatively define a measured gas chamber 239 around oxygen concentration sensing element 1. Numerous gas holes 230 and 233 are provided on element protectors 231 and 232, for introducing measured gas into the gas chamber 239.

The atmospheric cover 241 is fixed to the housing 20 by a caulking operation through a metallic ring 215. The atmospheric cover 242 is fixed to the atmospheric cover 241 by a caulking operation. The atmospheric cover 243 is also fixed to the atmospheric cover 241 by a caulking.

The oxygen concentration sensing element 1 is supported, at its flange portion 19, on a tapered portion formed on the inside surface of housing 20 through a metallic washer 211. Talc 212, pad 213, insulator 214 are successively accumulated in a space formed between the upper surface of flange portion 19 and the inside surface of housing 20, to provide a hermetric seal between them. The lower end of atmospheric cover 241 is brought into contact with insulator 214.

An output signal path of the oxygen concentration sensing element 1 will be explained hereinafter.

As shown in FIGS. 1A and 1B, in the solid electrolyte 10, external electrode 15 is electrically connected via external electrode lead 150 to external electrode terminal 151. An output signal of oxygen concentration sensing element 1 is taken out from a signal output portion 163 attached on the external electrode terminal 151. The signal output portion 163 comprises a contact piece directly brought into contact with external electrode terminal 151 and a terminal piece conductive to is contact piece.

Figure 10A:
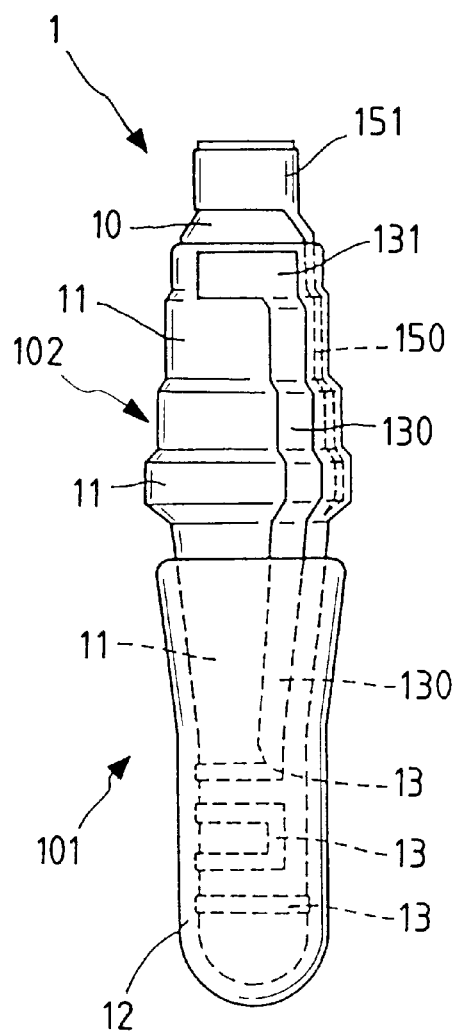
FIG. 10A is a side view showing a right side of an oxygen concentration sensing element in accordance with a fourth embodiment of the present invention.
Figure 10B:
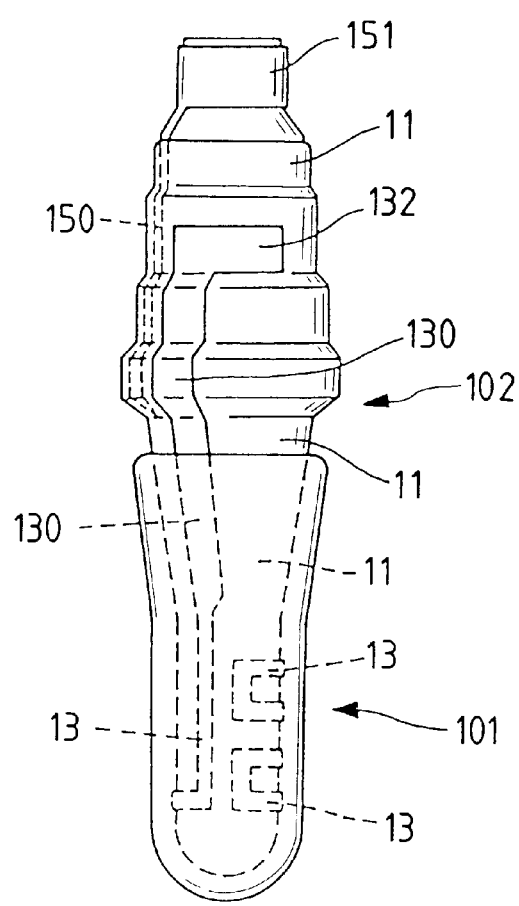
FIG. 10B is a side view showing a left side of the oxygen concentration sensing element in accordance with the fourth embodiment of the present invention.
Figure 11:
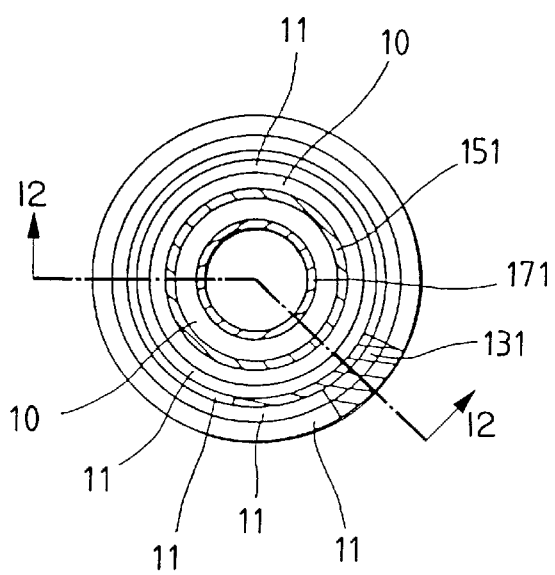
FIG. 11 is a cross-sectional plan view showing the oxygen concentration sensing element in accordance with the fourth embodiment of the present invention.
Figure 12:
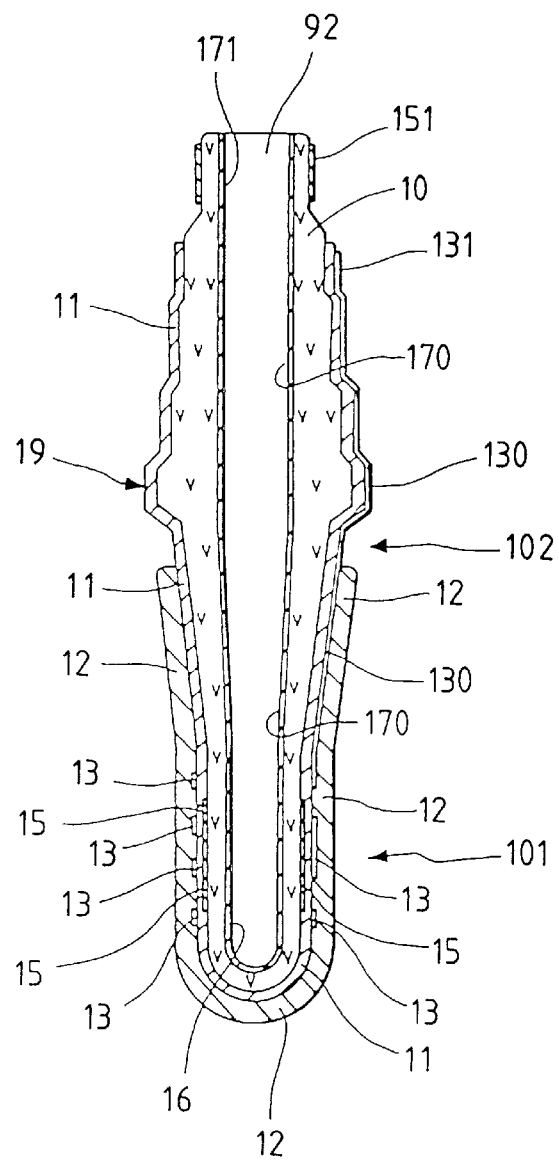
FIG. 12 is a vertical cross-sectional view taken along a line A—A of FIG. 11.

Meanwhile, in the solid electrolyte 10, the internal electrode 16 is electrically connected to an internal electrode terminal 171 via an internal electrode lead 170. These internal electrode terminal and the internal electrode lead are formed or provided along the inner wall surface of solid electrolyte 10 (refer to FIGS. 10, 11 and 12 and related descriptions).

The internal electrode terminal is provided separately from the external electrode terminal 151. A signal output portion 164 is attached on the oxygen concentration sensing element 1, such that the signal output portion 164 is brought into contact with this internal electrode terminal. The signal output portion 164 is a component independent of the signal output portion 163 connected to the external electrode teral 151.

Next, a current path of the heater layer 13 will be explained.

As shown in FIGS. 1A and 1B, the solid electrolyte 10 is provided with heater terminals 131 and 132 connected via heater leads 130 to the heater layer 13. To energize heater layer 13, positive and negative current terminals 161 and 162 are attached on the heater terminals 131 and 132, respectively. These positive and negative current terminals 161 and 162 comprise contact pieces brought into contact with these current terminals 161 and 162 as well as leads 166 and 167 conductive to these contact pieces.

The signal output portions 163, 164 and current terminals 161, 162 are connected to lead wires 171 to 174. These lead wires 171 to 174 extend through the inside space of atmospheric covers 241, 242 and 143 of oxygen concentration detector 2 and are held by a connector 29 provided outside the oxygen concentration detector 2.

The oxygen concentration detector 2 is fixedly installed, through a screw portion 201 formed on the housing 20, on a member of an exhaust system of an automotive vehicle's internal combustion engine.

Next, a manufacturing method of the above-described oxygen concentration sensing element 1 will be explained.

First of all, starting material, such as $ZrO_2$, is pressurized and molded into a cup-shaped configuration. Then, the molded material is baked at a temperature of 1,400° C. to 1,600° C., to obtain the cup-shaped solid electrolyte 10.

Internal electrode 16, external electrode 15, the electrode leads, and the electrode terminals are formed on the inner and outer wall surfaces of solid electrolyte 10 by a sputtering or plating noble metallic powder, such as Pt.

Subsequently, first insulating layer 11 is formed by plasma spraying heat-resistive metallic oxide powder on the outer wall surface of solid electrolyte 10 at a predetermined region below flange portion 19 and the surface of external electrode 15.

Then, heater layer 13, heater lead 130 and heater terminals 131, 132 are formed by printing electrically conductive paste on the outer wall surface of solid electrolyte 10 at a predetermined region above the flange 19 and the surface of first insulating layer 11 as shown in FIGS. 1A, 1B and 2 and thermally processing the same at a temperature of 900° C. to 1,100° C.

Next, second insulating layer 12 is formed by plasma spraying the above heat-resistive metallic oxide powder on the heater layer 13 and the first insulating layer 11.

Through the above processing, the oxygen concentration sensing element 1 is obtained.

The function and effect of the above-described first embodiment will be explained hereinafter.

According to the oxygen concentration detector 2 of the first embodiment, the sensing element 1 has heater layer 13 interposed between first insulating layer 11 and second insulating layer 12. The distance between heater layer 13 and solid electrolyte 10 is several hundreds μm at maximum. Hence, most of heat generated from heater layer 13 is transmitted quickly to solid electrolyte 10.

Furthermore, heater layer 13 is not provided directly on solid electrolyte 10. This arrangement is effective to prevent solid electrolyte 10 from being deteriorated by a reduction due to a leak current from heater layer 13.

Therefore, the first embodiment can adequately provide insulation between external electrode 15 and internal electrode 16 and heater layer 13. Furthermore, it becomes possible to provide the oxygen concentration detector 2 having the oxygen concentration sensing element 1 with an excellent warm-up ability.

Accordingly, the oxygen concentration detector 2 using the oxygen concentration sensing element 1 in accordance with the first embodiment of the present invention can detect an air-fuel ratio accurately even immediately after the internal combustion engine has started up.

Figure 6:
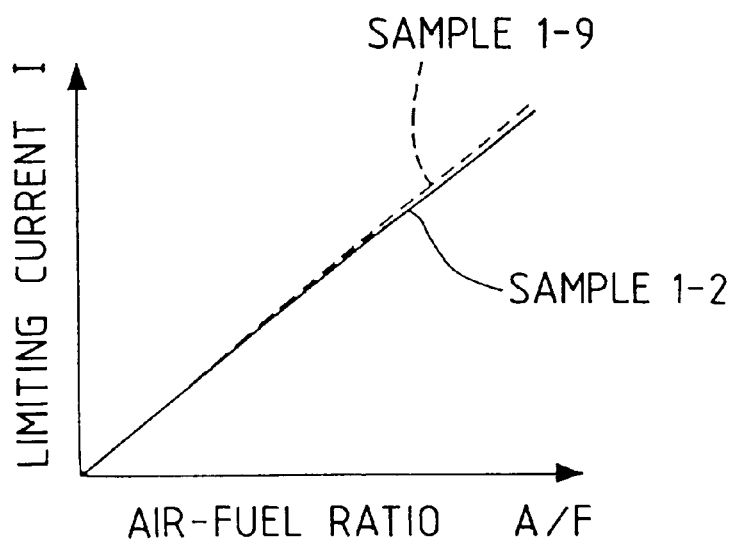
FIG. 6 is a graph showing a relationship between an air-fuel ratio and a limiting current in an oxygen concentration sensing element of the present invention and a conventional oxygen concentration sensing element.

FIG. 6 shows the relationship between the lifting current and the air-fuel ratio with respect to each of oxygen concentration sensing element 1 of the first embodiment (i.e., later-described sample 1-2 shown in Table 1) and the conventional oxygen concentration sensing element 9 of FIG. 28 (i.e., later-described sample 1-9 shown in Table 1). According to FIG. 6, there is no substantial difference between the first embodiment of the present invention and the conventional element.

Next, the characteristics of oxygen concentration sensing element 1 of the first embodiment of the present invention will be explained with reference to the evaluation result shown in Table 1.

In Table 1, samples 1-1 through 1-8 are oxygen concentration sensing elements manufactured in accordance with the first embodiment of the present invention, but are different in their thicknesses of the first insulating layer and H/D values. "H" represents an area of the heater layer covering the external electrode, while "D" represents an area of the external electrode used for the detection of oxygen concentration.

Figure 34:
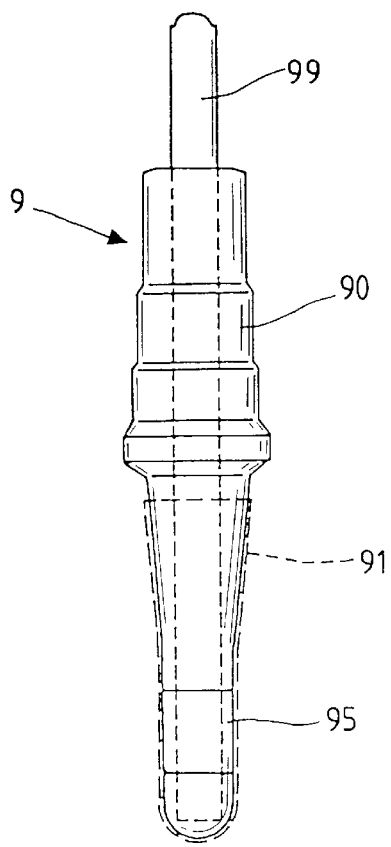
FIG. 34 is a side view showing a conventional oxygen concentration sensing element.
Figure 35:
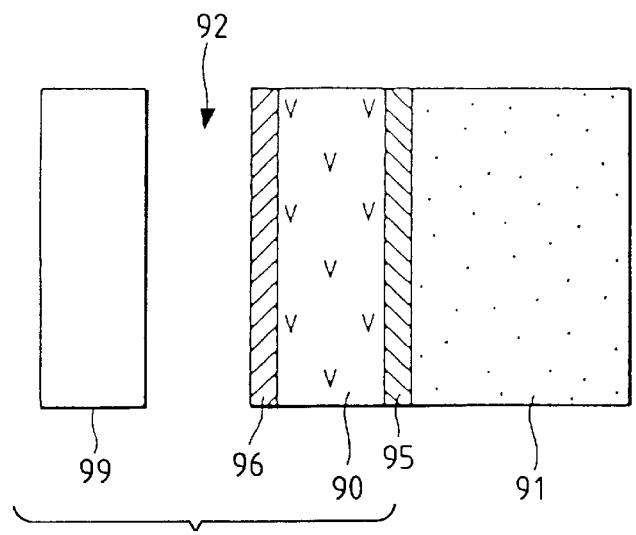
FIG. 35 is a vertical cross-sectional view showing an essential arrangement of the conventional oxygen concentration sensing element.
Figure 29:
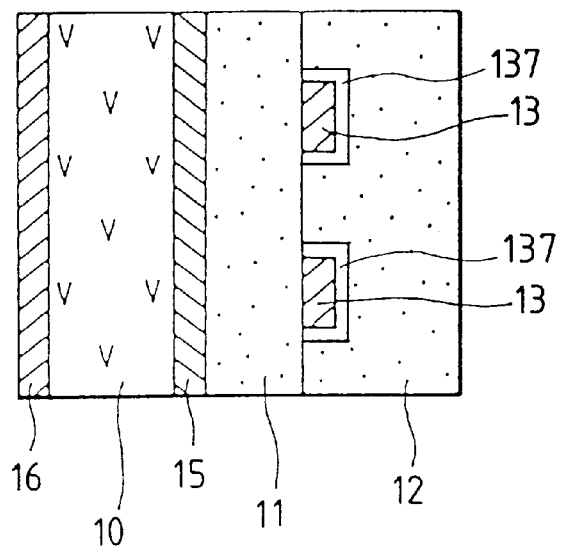
Figure 30:
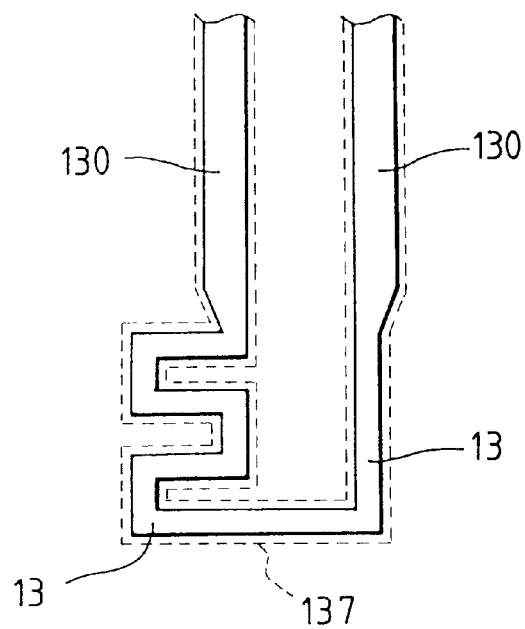

On the other hand, a sample 1-9 is oxygen concentration sensing element 9 shown in FIGS. 34 and 35 which comprises solid electrolyte 90, external electrode 95 provided on the outer wall surface of solid electrolyte 90, internal electrode 96 provided on the inner wall surface of solid electrolyte 90, and insulating layer 91 provided on the surface of external electrode 95. The oxygen concentration sensing element 9 comprises inside chamber 92 for introducing a reference gas. Round stick-like heater 99 is inserted into this inside chamber 92 and settled there. The heater 99 is formed by silicon nitride with a heater element involved therein.

The performance evaluation is conducted on each of "insulation ability", "response" and "warm-up ability".

In the evaluation on the "insulation ability", a resistance between the heater layer and the external electrode is measured at the normal temperature (20° C.±1° C.) with respect to each of the samples 1-1 through 1-8, and a resistance between the heater layer and the internal electrode is measured at the room temperature with respect to the sample 1-9. A sample having a resistance equal to or larger than 1 MΩ is denoted by "O", while a sample having a resistance less than 1 MΩ is denoted by "X".

In the evaluation on the "response", samples 1-1 to 1-9 are incorporated in the oxygen concentration detector (FIG. 4) which is installed on the exhaust system of a 2,000 cc, 6-cylinder engine. A fuel injection amount of an injector of this engine is widely varied, at an engine speed of 1,100 rpm/s, so as to switch the air-fuel ratio from 14 to 15 and vice versa to measure a response time of the oxygen concentration detector. A sample having a response time equal to or smaller than 200 ms is denoted by "O", while a sample having a response time larger than 200 ms is denoted by "X".

When an output current value of the above-described (lifting-current type) oxygen concentration causes a change of a width of 100 in response to the switch of the air-fuel ratio, the response time is defined as a time required to reach a 63% point of the entire change width from the moment the air-fuel ratio is switched.

The evaluation on the "warm-up ability" is conducted in the following manner.

A heater layer, having a normal-temperature resistance of 1 Ω, is equipped in the oxygen concentration sensing element of each of samples 1-1 through 1-9. The oxygen concentration detector incorporating this oxygen concentration sensing element is installed in an exhaust gas system of an engine. An electric voltage of 14V is applied on the oxygen concentration sensing element after the engine is started. An internal resistance of the oxygen concentration sensing element is measured by applying 0.1 v between the internal and external electrodes. A sample having an internal resistance equal to or smaller than 150 Ω is denoted by "O", while a sample having an internal resistance larger than 150 Ω is denoted by "X".

Furthermore, while the internal resistance is measured in the same manner, a time required to reach 150 Ω is measured. A sample having the measured time less than 10 seconds is evaluated as having an excellent "warm-up ability."

From the result of Table 1, samples 1-1 through 1-5 have adequate performances in all of the "insulation ability", "response" and "warm-up ability", and therefore their excellent performances as oxygen concentration sensing element are confirmed. Sample 1-6 has a poor "response" due to its large H/D value. Sample 1-7 has a poor "insulation ability" due to the small thickness of its first insulating layer. Sample 1-8 has a poor "warm-up ability" due to the large thickness of its first insulating layer. Regarding sample 1-9, its "wardup ability" was unsatisfactory since its round-stick heater is provided independently from the oxygen concentration sensing element.

From the above experimental results, it is concluded that an excellent oxygen concentration sensing element can be obtained by setting the first insulating layer thickness somewhere in a range of 10–900 μm and setting the H/D value in a range of 0.1–0.8.

Figure 7:
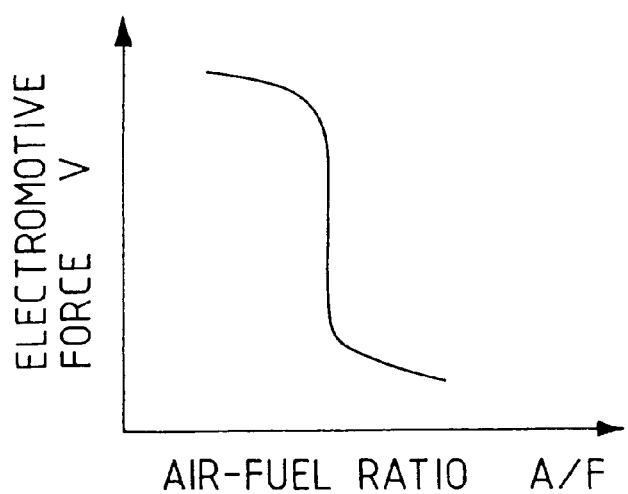
FIG. 7 is a graph showing a relationship between an air-fuel ratio and an electromotive force in an oxygen concentration cell type oxygen concentration sensing element in accordance with the first embodiment of the present invention.

FIG. 7 shows an oxygen concentration cell type oxygen concentration sensing element producing an output signal (i.e., electromotive force) rapidly changing at a critical point corresponding to a theoretical air-fuel ratio. The heater arrangement of the first embodiment can also be applied to such an oxygen concentration cell type oxygen concentration sensing element. Similar function and effect can be obtained.

FIGS. 8A and 8B show a modification of the layout of external electrode 15 wherein the area of external electrode 15 is extended so as to cover the lower portion and the bottom of solid electrolyte 10. Substantially the same function and effect as those described above can be obtained even in such a modified oxygen concentration sensing element.

TABLE 1

| Sample No. | 1st insulating layer thickness | H/D value | Insulation ability | Response | Warm-up ability [time to reach 150Ω (s)] |
|---|---|---|---|---|---|
| 1-1 | 10 | 0.4 | O | O | O [4] |
| 1-2 | 200 | 0.4 | O | O | O [5] |
| 1-3 | 900 | 0.4 | O | O | O [9] |
| 1-4 | 200 | 0.1 | O | O | O [5] |
| 1-5 | 200 | 0.8 | O | O | O [5] |
| 1-6 | 200 | 0.9 | O | X | O [5] |
| 1-7 | 5 | 0.4 | X | O | O [4] |
| 1-8 | 1000 | 0.4 | O | O | X [10] |
| 1-9 | — | 0.4 | O | O | X [10] |

As apparent from the foregoing description, the first embodiment of the present invention provides an air-fuel ratio sensing element comprising a solid electrolyte formed into a cup-shaped configuration with one end opened and the other end closed, an external electrode provided on an outer wall surface of the solid electrolyte so as to be exposed to measured gas, and an internal electrode provided on an inner wall surface of the solid electrolyte in a confronting relationship to the external electrode. Furthermore, a first insulating layer is provided on the external electrode at least in a region used for detection of an air-fuel ratio. This first insulating layer is formed by a gas-permeable and electrically nonconductive porous material. A second insulating layer is provided outside the first insulating layer. This second insulating layer is nonconductive. A heater layer is provided between the first insulating layer and the second insulating layer.

According to the first embodiment of the present invention, the heater layer is provided between the first insulating layer and the second insulating layer. The distance between the heater layer and the solid electrolyte is in a level of hundreds $\mu$m or less. Accordingly, most of thermal energy generated from the heater can be transmitted quickly and effectively to the external electrode. Thus, it becomes possible to obtain an air-fuel sensing element having an excellent warm-up ability.

Furthermore, the heater layer is covered by the second insulating layer. This is effective to reduce the amount of thermal energy lost to the outside without being used to warm up the electrode.

Moreover, the heater layer is not directly brought into contact with the solid electrolyte. This is effective to prevent the solid electrolyte from being subjected to a deteriorative reduction.

Accordingly, according to first embodiment of the present invention, it becomes possible to obtains an excellent air-fuel sensing element capable of preventing an insulation breakdown between the external electrode and the internal electrode, and having a satisfactory warm-up ability.

It is preferable to provide the heater layer covering a 10–80% area of the external electrode.

To enhance the warm-up ability, it is preferable to provide the heater layer on the external electrode. However, the heater layer has a tendency of intercepting oxygen passing therethrough. Hence, the oxygen concentration sensing ability of the external electrode may be deteriorated locally at a portion beneath the heater layer.

In other words, when the heater layer covers the external electrode at a rate less than 10%, the distance between the heater layer and the external electrode becomes too long to assure a satisfactory warm-up ability of the air-fuel ratio sensing element. On the other hand, when the heater layer covers the external electrode at a rate larger than 80%, oxygen is intercepted by the heater layer and therefore the accuracy of the oxygen concentration detection deteriorates undesirably.

In the above description, the area of the external electrode is an area of a portion actually used for detection of oxygen concentration. More specifically, as shown in FIG. 4, this area corresponds to a portion facing to the measured gas chamber.

In the air-fuel ratio sensing element, thermal energy generated from the heater layer is transferred from the closed end portion to the barrel portion of the air-fuel ratio sensing element. This transfer of thermal energy causes a temperature distribution gradually reducing from the closed end portion to the barrel portion.

In view of the above, it is preferable to reduce the width of the heater layer at the side closer to the barrel portion. Otherwise, it is preferable to reduce the thickness of the heater layer at the side closer to the barrel portion. Furthermore, it is preferable to form the heater layer having a pattern concentrated to the barrel portion so as to increase the temperature of the barrel portion.

With the above-described arrangements, it becomes possible to increase the heat generation amount at the barrel portion side. Thus, the undesirable temperature distribution can be eliminated adequately.

Furthermore, the first embodiment of the present invention provides an air-fuel ratio sensor comprising an air-fuel ratio sensing element and a housing accommodating this air-fuel ratio sensing element therein. The air-fuel ratio sensor of the present invention can be arranged in various ways. For example, as disclosed in FIG. 4, the air-fuel ratio sensor comprises a housing fixedly supporting an oxygen concentration sensing element, an element protector covering the tip end (closed end, or lower end) of this oxygen concentration sensing element, and an atmospheric cover provided at the opposite end.

In this case, the oxygen concentration (i.e., air-fuel ratio) sensing element can be directly supported by the housing, or indirectly supported by the housing via a metallic washer.

Furthermore, talc and an insulator can be accumulated between the oxygen concentration sensing element and the housing. This arrangement is advantageous to provide an airtight sealing between the oxygen concentration sensing element and the housing, while providing an appropriate insulation property between them.

It is preferable that the second insulating layer is made of a gas-permeable porous material, so that measures gas can smoothly penetrate the second insulating layer and quickly reach the external electrode. Thus, an air-fuel ratio sensor having an excellent response can be obtained.

Furthermore, it is preferable that the first insulating layer has a thickness of 10–900 $\mu$m and a porous rate of 1–50%, to provide an air-fuel ratio sensing element having a reliable insulation property and an excellent response. If the thickness of the first insulating layer is less than 10 $\mu$m, the detection of oxygen concentration will fail because the gap between the heater layer and the solid electrolyte becomes too narrow to maintain the insulation property. On the other hand, if the thickness of the first insulating layer exceeds 900 $\mu$m, warning up the external electrode will be delayed because the gap between the heater layer and the external electrode is increased excessively. When the porous rate of the first insulating layer is less than 1%, the gas diffusibility in the first insulating layer may be worsened. On the other hand, when the porous rate of the first insulating layer exceeds 50%, the mechanical strength of the first insulating layer may be reduced and cracks or the like may be caused when subjected to vibrations or shocks. Furthermore, the first insulating layer may peel off. Also, the insulation ability of the first insulating layer may worsened.

Furthermore, the first insulating layer and the second insulating layer can be formed by plasma spraying the powder of a heat-resistive metallic oxide, such as aluminum and spinel.

A heat-resistive metallic oxide having a higher heat conductivity, such as MgO or BeO, is preferably used for the first insulating layer. Meanwhile, a heat-resistive metallic oxide having a lower heat conductivity, such as cordierite or mullite, is preferably used for the second insulating layer. Selecting this combination for determining the materials of the first insulating layer and the second insulating layer is effective to prevent the thermal energy of the heater from being lost from the surface of the oxygen concentration sensing element.

Regarding the material of the heater layer, it is preferable that the heater layer is made of an electrically conductive material and hyaline. The electrically conductive material serves as heater means for generating heat. The hyaline serves as bonding means for bonding the electrically conductive material to the surface of the first insulating layer. Thus, a heater layer having a strong adhesive force against the first insulating layer can be obtained. In this case, the hyaline comprises borosilicate glass and flint glass.

In forming the heater layer, it is preferable to prepare electrically conductive paste by mixing the electrically conductive material and the hyaline together with an organic solvent, and then applying this paste on the surface of the first insulating layer by using printing or equivalent technology. Through this fabrication method, the heater layer can be formed into a desired pattern.

In adjusting the conductive paste, it is preferable to mix the electrically conductive material of 50–90 weight % and hyaline of 1–20 weight % together with organic solvent, and organic binder if necessary, to obtain the conductive paste of 100 weight %. Using this electrically conductive paste makes it possible to form a heater layer having a uniform thickness and a strong adhesive force against the first insulating layer.

If the conductive material is less than 50 weight %, a large amount of shrinkage will occur during a baking operation, causing cracks in the heater layer. Thus, it is difficult to obtain a stable layer. On the other hand, if the conductive material is larger than 90 weight %, the viscosity of the conductive paste become too large. This may cause blurring or unevenness during a printing operation.

When the rate of hyaline is less than 1 weight %, there is a possibility that the adhesive force of the heater layer may be deteriorated by a thermal processing. On the other hand, when the contained rate of hyaline exceeds 20 weight %, there is a possibility that the resistance value of the heater layer may become an excessively large value.

Furthermore, it is preferable that the electrically conductive material is a power having a particle size of 0.1–5 $\mu$m. By using such power, an excellent heater layer can be obtained.

When the particle size of the electrically conductive material is less than 0.1 $\mu$m, there is a possibility that the electrically conductive material may aggregate by the thermal processing. On the other hand, when the particle size of the electrically conductive material is larger than 5 $\mu$m, there is a possibility that the electrical resistance of the heater layer may become an excessively large value.

The printing operation of the heater layer can be performed by using a screen printing technology, a pad printing technology, or a roll transfer technology.

It is possible to prepare a transfer sheet comprising electrically conductive paste layer and an adhesive layer accumulated on his paste layer. This transfer sheet is affixed on the first insulating layer by placing the adhesive layer downward, thereby forming a heater layer.

A benefit of using such a transfer sheet is that the thickness of the heater layer can be controlled accurately. If the thickness of the heater layer is dispersed, an initial resistance value of the heater layer is dispersed correspondingly. Furthermore, the durability of the heater layer may be worsened. The above-described method can solve such problems.

Next, it is preferable that the heater layer is formed by an electrically conductive material, and the electrically conductive material contains either a noble metallic powder, such as Pt, Rh and Pd, or a perovskite type oxide powder, such as $LaCrO_3$ and $La_{0.5}Sr_{0.5}CoO_3$. It is advantageous to obtain a heater layer having an excellent durability. Using perovskite type oxide powder is effective to reduce the material cost of the heater layer.

Furthermore, it is preferable that the heater layer is made of a metallic wire or metallic foil, such as kanthal, because the material costs of the heater can be reduced and the dispersion of the resistance value can be reduced.

When the metallic wire is used, the metallic wire is rolled in a coil shape. Then, the solid electrolyte with the first insulating layer is inserted into this coil-shaped metallic wire and baked together to form a heater layer.

Furthermore, it is preferable that the air-fuel ratio sensing element of the present invention further comprises a heater lead connected to the heater layer, an external electrode lead connected to the external electrode, and an internal electrode lead connected to the internal electrode. The heater lead, external electrode and internal electrode are provided along the wall surfaces of the solid electrolyte.

With this arrangement, it becomes possible to form the heater layer, the internal electrode and the external electrode at their respective intended portions flexibly. Thus, high performance and low costs are assured, and the signal processing and the electric power supply can be facilitated.

It is still preferable that the solid electrolyte have a closed end portion closer to the bottom thereof and a barrel portion formed at an intermediate portion. In this case, the heater is provided in a predetermined region of the closed end portion while a heater terminal is provided on the barrel portion, and the heater terminal is connected to the heater layer via a heater lead. The first insulating layer is formed on the outer wall surface of the solid electrolyte so as to extend to a region of the heater terminal.

When the air-fuel ratio sensor of the present invention is installed in an exhaust gas system of an internal combustion engine for an automotive vehicle, especially at a portion closer to a combustion chamber of this engine, the air-fuel ratio sensor is possibly exposed to a high-temperature exhaust gas. The closed end portion of the solid electrolyte, i.e., a portion where the external electrode is provided, may be heated severely by the thermal energy of exhaust gas in addition to the heat generated from the heater layer. The heat accumulated in the closed end portion is transmitted to the barrel portion of the solid electrolyte. Thus, the barrel portion is heated to a higher temperature.

In such a severe temperature condition, it is preferable to extend the region of the first insulating layer to the heater terminal to prevent the solid electrolyte from being deteriorated by the reduction at the barrel portion. This is also effective to prevent the insulation breakdown between the solid electrolyte and the heater layer.

The first insulating layer formed at the barrel portion does not need to identical with the first insulating layer formed at the closed end portion. More specifically, the first insulating layer in the region of the closed end portion needs to have a sufficient gas permeability to guide the measured gas to the solid electrolyte. However, the first insulating layer in the region of the barrel portion does not need to have a comparable gas permeability. Hence, it is possible to reduce the porous rate of the first insulating layer provided in the region of the barrel portion.

The air-fuel sensing element of the present invention is accommodated in a housing to constitute an air-fuel ratio sensor. In this case, the air-fuel ratio sensing element can be directly supported by the housing. According to this supporting method, the air-fuel ratio sensing element is stably and accurately assembled into the housing without causing interference between the components attached on the surfaces of the air-fuel sensing element, such as signal output members and heater lead members (refer to FIG. 4) and the covers or the like of the air-fuel sensing element (refer to FIG. 4).

It is also preferable that the air-fuel ratio sensing element is indirectly supported by the housing via a metallic washer. With this arrangement, a large shock is applied directly to the solid electrolyte is prevented when installed in the housing.

Furthermore, it is preferable that the air-fuel ratio sensing element is indirectly supported by the housing via an insulator. With this arrangement, external noises entering into the oxygen concentration detection circuit are prevented. Furthermore, a heat transfer from the heater layer to the housing is prevented.

Yet further, it is preferable that the second insulating layer is formed along the outer surface of the first insulating layer so as to extend to a region where the air-fuel ratio sensing element is supported to the housing. This is advantageous to prevent the thermal energy of the heater not being lost through the supporting surface to the housing. No special arrangement is required for providing an electrical insulation between the heater layer and the housing. The total number of parts can be reduced. Hence, the arrangement of the air-fuel ratio sensing element is simplified.

Furthermore, it is preferable that the heater layer has an oxygen absorbing force weaker than that of the external electrode.

In the oxygen concentration sensing element disclosed in the first embodiment, oxygen contained in the measured gas reaches the external electrode via the second insulating layer and the first insulating layer (or only the first insulating layer at a region where the second insulating layer is not provided).

Accordingly, there is a possibility that the oxygen contained in the measured gas may pass near the heater layer on the way to the external electrode.

If the heater layer has an oxygen absorbing force larger than that of the external electrode, a significant amount of oxygen contained in the measured gas will be trapped by the heater layer. In this case, an arrival of the oxygen to the external electrode will be delayed. Hence, the response of the oxygen concentration sensing element is lowered.

From the foregoing reasons, reducing the oxygen absorbing force of the heater layer to a value smaller than that of the external electrode is effective to prevent the oxygen contained in the measured gas from being trapped by the heater layer. Thus, an oxygen concentration sensing element having an excellent response can be obtained.

Furthermore, it is preferable that the heater layer is made of an alloy comprising platinum and gold, with a mixing rate of the gold in a range of 0.5–50 weight %. This is advantageous to weaken the oxygen absorbing force of the heater layer compared with that of the external electrode.

The external electrode is made of noble metal including platinum, other than gold.

When the rate of gold is less than 0.5 weight %, it is difficult to reduce the oxygen absorbing force of the heater layer. The response of the air-fuel ratio sensor is worsened. On the other hand, when the rate of gold exceeds 50 weight %, the melting point of the heater layer is remarkably lowered to a value close to an ordinary temperature range of the activated heater layer. This will lead to a deterioration of the heater layer.

In forming the heater layer, as described above, it is preferable to prepare electrically conductive paste by adding organic solvent to the electrically conductive material and hyaline, and apply this paste on the surface of the first insulating layer by printing or equivalent technology.

The adjustment of the conductive paste for heater layer can be done by the following methods.

According to a first method, platinum powder and gold powder are mixed at a predetermined ratio. Then, the resultant power mixture is further mixed with frit-containing powder together with organic binder and organic solvent by using a kneading method, thereby obtaining the conductive paste.

According to a second method, an alloy of platinum and gold with a predetermined ratio is formed. Then, the power of the resultant alloy is further mixed with frit-containing powder together with organic binder and organic solvent by using a kneading method, thereby obtaining the conductive paste According to a third method, organic salt containing gold is mixed with platinum powder. Then, the resultant mixture is further mixed with frit-containing powder together with organic binder and organic solvent by using a kneading method, thereby obtaining the conductive paste.

According to a fourth method, organic salt containing gold is mixed with organic salt containing platinum. Then, the resultant mixture is further mixed with frit-containing powder together with organic binder and organic solvent by using a kneading method, thereby obtaining the conductive paste.

According to a fifth method, platinum powder is mixed with the organic salt containing gold and platinum. Then, the resultant mixture is further mixed with frit-containing powder together with organic binder or organic solvent by using a kneading method, thereby obtaining the conductive paste.

Regarding the material of the heater layer, it is preferable that the heater layer contains platinum and at least one component selected from the group consisting of Pd, Rh and Ir. This is advantageous to weaken the oxygen absorbing force of the heater layer.

Moreover, it is preferable that the heater lead and the external electrode lead have a catalytic action of oxidation and reduction to the measured gas smaller than that of the external electrode.

According to the air-fuel ratio sensing element of the present invention, measured gas may reach the heater lead and the external electrode lead. In this case, HC, CO, $CO_2$ or the like contained in the measured gas are cooled down and are possibly oxidized or reduced and thus deposited as carbon. This will result in the deterioration of the heater lead and the external electrode lead.

Accordingly, reducing the catalytic action of the heater lead and the external electrode lead is effective to suppress the deposition of carbon and accordingly to prevent the heater lead and the external electrode lead from being deteriorated or broken.

Regarding the material of heater lead, it is preferable that the heater lead is made of gold, or by an alloy containing gold and at least one component selected from the group consisting of Pt, Pd, Rh and Ir. This is advantageous to reduce the catalytic action of the heater lead and the external electrode lead. Namely, the deposition of carbon is effectively suppressed, thus preventing the deterioration and breakage of the heater lead and the external electrode lead. Furthermore, it becomes possible to reduce the electric resistance of the heater lead to a value smaller than that of the heater layer. If the heater layer and the heater lead are made of the same material, their electric resistance values become comparable. In such a case, upon supplying electric current, both of the heater layer and the heater lead generate heat. The heat generated at the heater lead does not contribute to warm up the external electrode. Hence, the part of electric power is wasted.

However, constituting the heater lead by gold or by an alloy of gold is effective to reduce the electric resistance of the heater lead and concentrate the heat generation at the heater layer. Accordingly, electric power supplied to the heater layer via the heater lead can be effectively used for warming up the external electrode.

In forming the heater lead, it is preferable to prepare electrically conductive paste by adding organic solvent, and organic binder if necessary, to the mixture of the electrically conductive material and the hyaline and then applying the resultant paste on the surface of the first insulating layer by a printing or equivalent technology.

Regarding the adjusting method of the conductive paste used for forming the heater lead, the following methods will be used.

According to a first method, frit-containing powder is mixed with organic binder and organic solvent by using a kneading method, thereby obtaining the conductive paste.

According to a second method, gold is mixed with at least one component selected from the group consisting of Pt, Pd, Rh and Ir at a predetermined mixing ratio, to form an alloy. The powder of the resultant alloy is then mixed with a frit-containing powder together with organic binder and organic solvent by using a kneading method, thereby obtaining the conductive paste.

According to a third method, a powder of gold is mixed with platinum-containing organic salt. Then, the resultant mixture is then mixed with a frit-containing powder together with organic binder and an organic solvent by using a kneading method, thereby obtaining the conductive paste.

According to a fourth method, organic salt containing gold is mixed with an organic salt containing platinum or the like. Then, the resultant mixture is further mixed with frit-containing powder together with an organic binder and organic solvent by using a kneading method, thereby obtaining the conductive paste.

According to a fifth method, a gold powder is mixed with the organic salt containing gold and platinum. Then, the resultant mixture is further mixed with a frit-containing powder together with an organic binder and organic solvent by using a kneading method, thereby obtaining the conductive paste.

Second Embodiment

A second embodiment of the present invention provides an oxygen concentration sensing element different in its manufacturing method from that of the first embodiment.

First, a powder of starting material, such as $ZrO_2$, is pressurized and molded into a cup-shaped configuration and then baked at a temperature of 1,200° C. temporarily, to obtain the cup-shaped solid electrolyte 10.

Next, platinum powder having a particle size of 0.1–5 µm, by a 50–90 weight %, is mixed with hyaline powder of 1–10 weight %. The resultant mixture is then mixed with an organic binder of 3–10 weight % together with an organic solvent to obtain electrically conductive paste of 100 weight %.

Subsequently, the internal electrode 16 and external electrode 15, the electrode leads, and the electrode terminals are formed by printing the prepared conductive paste on the inner and outer wall surfaces of the solid electrolyte 10 and drying the same.

Subsequently, the first insulating layer 11 is formed by dipping a slurry of heat-resistive metallic oxide powder on the outer wall surface of the solid electrolyte 10 at a region below its flange 19 and the surface of the external electrode 15 (refer to FIGS. 1A and 1B) and then drying the same. Alumina and spinel are examples of the heat-resistive metallic oxide powder.

Then, the heater layer 13, the heater lead 130 and the heater terminals 131, 132 are formed by printing the electrically conductive paste on the outer wall surface of the solid electrolyte 10 at a region above the flange 19 and the surface of the first insulating layer 11 (refer to FIGS. 1A and 1B) and drying the same.

Finally, this solid electrolyte is baked at a temperature of 1,400° C.–1,600° C. to obtain an oxygen concentration sensing element. Arrangements are similar to those of the first embodiment. Functions and effects substantially the same as the first embodiment can be obtained.

Third embodiment

A third embodiment of the present invention provides an oxygen concentration sensing element having an air gap layer around a heater layer, as shown in FIG. 9.

An insulating layer 18 of the oxygen concentration sensing element comprises a first insulating layer 11 provided on the surface of external electrode 15, a second insulating layer 12 provided outside the first insulating layer 11, and a heater provided between these first and second insulating layers 11 and 12.

An air gap layer 139 is provided around the heater layer 13. This air gap layer is formed in the following manner.

Resin is applied on the heater layer 13 having been thus formed. Then, the second insulating layer 12 is formed on is resin by a plasma spray. Thereafter, the resin is removed through a baking operation. As a result, a space having been occupied by the resin is changed into a vacant space serving as air gap layer 139 surrounding the heater layer 13. Other arrangements are similar to those disclosed in the first embodiment.

The second insulating layer 12 of the oxygen concentration sensing element of the third embodiment is formed by a spinel material. On the other hand, the heater layer 13 is made of an electrically conductive material. Hence, there is a large thermal expansion difference between them. However, according to the arrangement of the third embodiment, any volumetric expansion of heater layer 13 can be absorbed by the air gap layer 139. In other words, the second insulating layer 12 is free from cracks or damage caused by thermal stresses. Other arrangements are substantially similar to those disclosed in the first embodiment.

Fourth embodiment

A fourth embodiment of the present invention provides an oxygen concentration sensing element having a first insulating layer extending to the proximity of a heater terminal, as shown in FIGS. 10A through 13.

As shown in FIGS. 10A through 12, an oxygen concentration sensing element 1 of the fourth embodiment comprises a cup-shaped solid electrolyte 10. An external electrode 15, an external electrode lead 150, and an external electrode terminal 151 are provided on the outer wall surface of solid electrolyte 10. An internal electrode 16, an internal electrode lead 160, and internal electrode terminal 161 are provided on the inner wall surface of solid electrolyte 10. A first insulating layer 11 is provided on the outer wall surface of solid electrolyte 10, with its lower portion covering the closed end portion 101 of solid electrolyte 10, its middle portion covering the barrel portion 102 of solid electrolyte 10, and its upper portion extending to the proximity of external electrode terminal 151.

A heater layer 13 is provided on the surface of the first insulating layer 11 at a region corresponding to the closed end portion 101 and outside the external electrode 15. Heater layer 13 is electrically connected via heater lead 130 to heater terminal 131, which are provided along the surface of barrel portion 102 of solid electrolyte 10.

Then, a second insulating layer 12 is accumulated on the first insulating layer 11 so as to cover the heater layer 13. The second insulating layer 12 is provided to cover a lower region of the solid electrolyte 10 below the flange portion 19. Other arrangements are substantially similar to those of the first embodiment.

According to the oxygen concentration sensing element of the fourth embodiment, the region of first insulating layer 11 is enlarged so that the upper end of the first insulating layer 11 reaches the heater terminal 131. With this arrangement, it becomes possible to prevent the solid electrolyte, at its barrel portion 102, from being subjected to a deteriorative reduction and insulation breakdown due to the provided heat and electrical potential. Other arrangements are substantially similar to those of the first embodiment.

A housing (refer to FIG. 4), used for fixedly accommodating the above oxygen concentration sensing element 1, is a metallic component. According to the fourth embodiment, to prevent the oxygen concentration sensing element 1 from being directly brought into contact with the housing, the oxygen concentration sensing element 1 is covered by a 50 μm thick ceramic layer extending in a predetermined region excluding the heater terminal 131.

Figure 13:
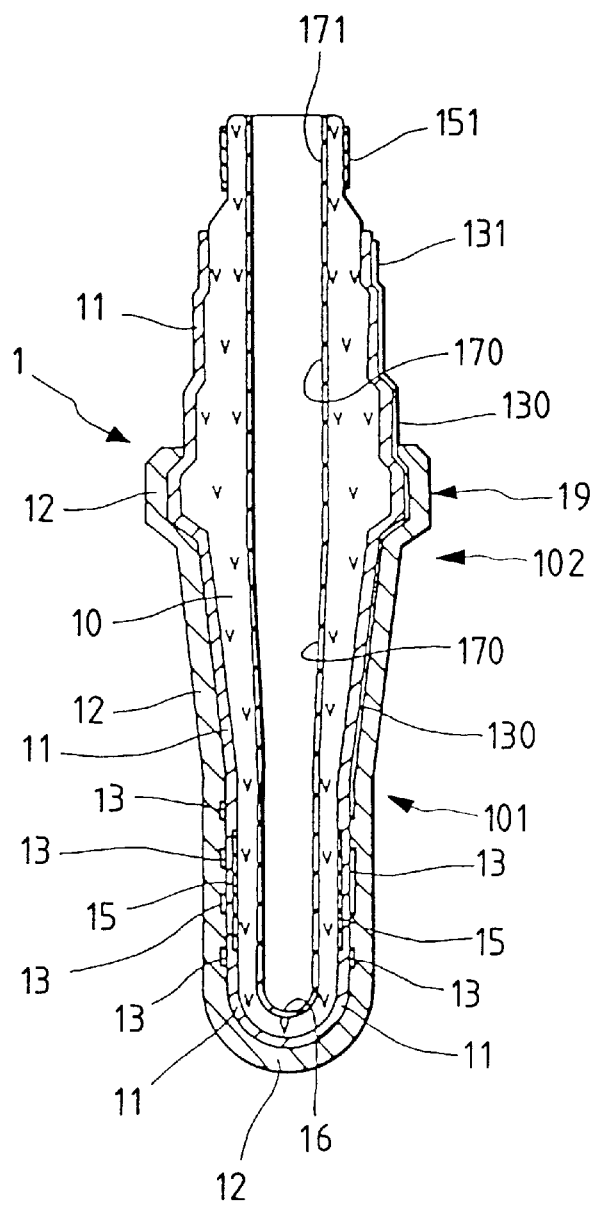
FIG. 13 is a vertical cross-sectional view similar to FIG. 12 but showing another oxygen concentration

FIG. 13 shows a modification of the fourth embodiment, according to which the second insulating layer 12 extends further upward to cover the flange portion 19 entirely. This arrangement is advantageous to prevent the heater lead from being brought directly into contact with the housing.

Fifth embodiment

A fifth embodiment of the present invention provides an oxygen concentration sensing element having a second insulating layer made of a gas impervious material.

Figure 14:
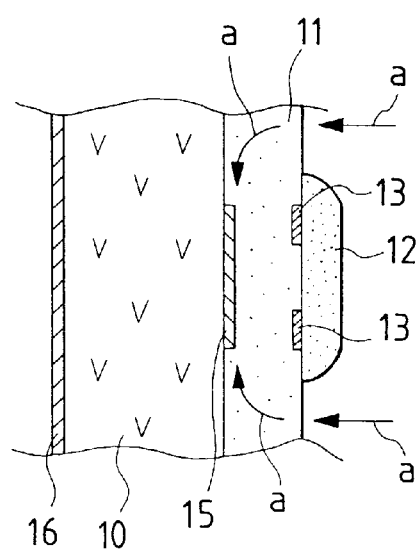
FIG. 14 is a vertical cross-sectional view showing an essential arrangement of an oxygen concentration sensing element in accordance with a fifth embodiment of the present invention.

As shown in FIG. 14, the oxygen concentration sensing element of the fifth embodiment comprises a solid electrolyte 10, an external electrode 15 provided on the outer wall surface of the solid electrolyte 10, and an internal electrode 16 formed on the inner wall surface of the solid electrolyte 10. A first insulating layer 11, which is made of a gas-permeable and electrically nonconductive porous material, is provided on the external electrode 15 at least in a region used for the detection of oxygen concentration.

A second insulating layer 12, which is made of a gas impervious and electrically nonconductive material, is provided outside the first insulating layer 11.

A heater layer 13 is provided between the first insulating layer 11 and the second insulating layer 12. The second insulating layer 12 is provided within a limited region corresponding to the heater layer 13. Other arrangements are substantially similar to those of the first embodiment.

The oxygen concentration sensing element of the fifth embodiment does not allow measured gas to penetrate the second insulating layer 12. Hence, the measured gas is introduced directly into the first insulating layer 13 and guided toward the external electrode 15 along a path detouring the second insulating layer 12 as indicated by an arrow "a" in FIG. 14.

As the second insulating layer 12 is provided only the region corresponding to the heater layer 13, the measured gas can be correctly guided to the external electrode 15 detouring the heater layer 13.

With this arrangement, it becomes possible to prevent oxygen involved in the measured gas from being absorbed by the heater layer 13. In other words, oxygen in the measured gas can reach the external electrode without delay. Thus, an oxygen concentration sensing element having an excellent response can be obtained.

Sixth embodiment

A sixth embodiment of the present invention provides an oxygen concentration sensing element having a heater layer provided on a flush surface formed on the first insulating later.

As shown in FIGS. 15A through 15D, the oxygen concentration sensing element comprise a cup-shaped solid electrolyte 10, an external electrode 15 provided on the outer wall surface of solid electrolyte 10, and an internal electrode 16 provided on the inner wall surface of solid electrolyte 10.

A first insulating layer 11 is provided on the external electrode 15 at least in a region used for the detection of oxygen concentration. A second insulating layer 12 is provided outside the first insulating layer 11. A heater layer 13 is interposed between the first insulating layer 11 and the second insulating layer 12.

A flush surface 110, having a surface roughness of 25 μas a mean value of ten measurement points (JIS B0601-1982), is formed on part of the outer surface of the first insulating layer 11. A tapered portion 19 is provided between the flush surface 110 and an uneven surface 111 of the first insulating layer 11.

A manufacturing method of the sixth embodiment will be explained hereinafter.

First, in the same manner as in the first embodiment, a cup-shaped solid electrolyte 10 is formed. Internal electrode 16, external electrode 15 and other components are formed on the inner and outer wall surfaces of this solid electrolyte 10.

After that, first insulating layer 11 is formed on the outer wall surface of the solid electrolyte 10 and the surface of external electrode 15.

Figure 15A:
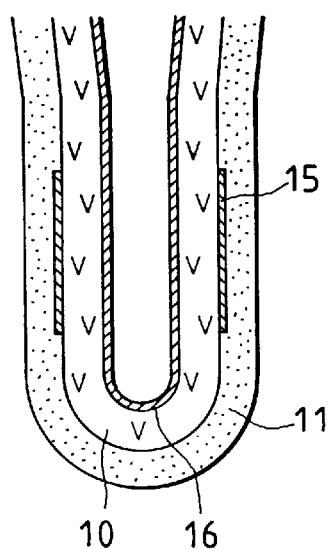
FIGS. 15A–15D are vertical cross-sectional views showing manufacturing processes of an oxygen concentration sensing element in accordance with a sixth embodiment of the present invention.
Figure 15B:
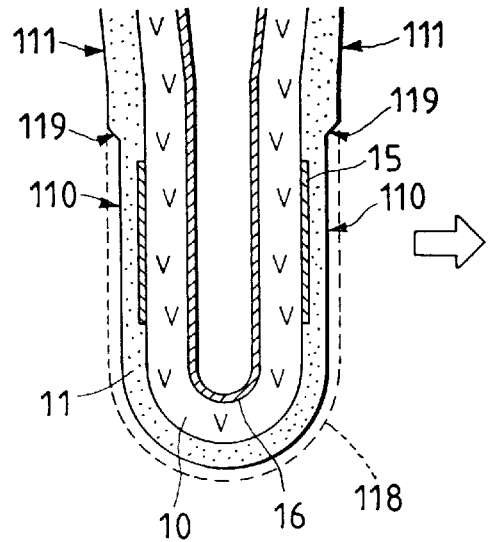

Next, as shown in FIG. 15A, part of the surface of first insulating layer 11 is cut by an appropriate machining tool, such as a diamond grindstone, at a predetermined lower region of the solid electrolyte 10. With the appropriate cutting, as shown in FIG. 15B, a surface portion 118 is partly removed from the first insulating layer 11, thereby forming glush surface 110. The tapered portion 119 is provided to prevent any stepped portion from being produced between the flush surface 110 and the uneven surface 111.

Figure 15C:
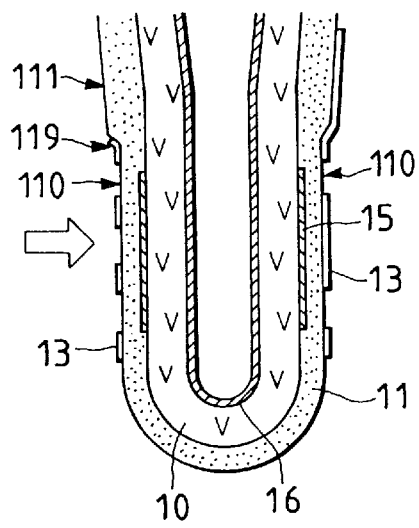
Figure 15D:
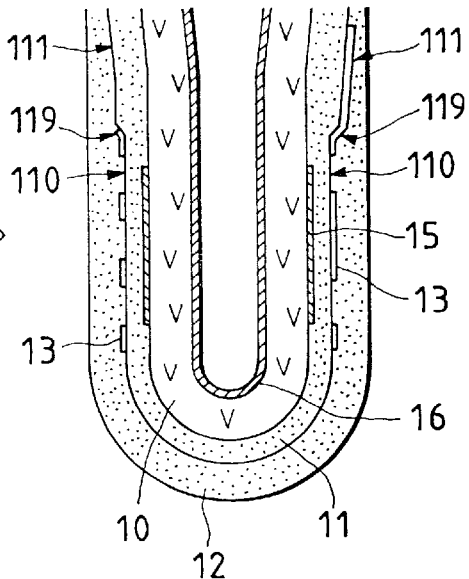

Thereafter, in the same manner as in the first embodiment, as shown in FIG. 15C, heater layer 13 and others are formed. Subsequently, as shown in FIG. 15D, second insulating layer 12 is provided. Other arrangements are substantially the same as those disclosed in the first embodiment.

Next, the effect of flush surface 110 of oxygen concentration sensing element will be explained in relation to the durability of heater layer 13, using samples a–c of the present invention and comparative samples C-a and C-b.

Each of samples a–c has a flush surface 110 whose surface roughness is 25 μm as a mean value of ten measured points. Heater layer 13 is provided on this flush surface 110.

Comparative samples C-a and C-b have first insulating layer 11 whose surface is not processed in a particular manner. The surface roughness of these comparative samples C-a and C-b is 45 μm.

Figure 16:
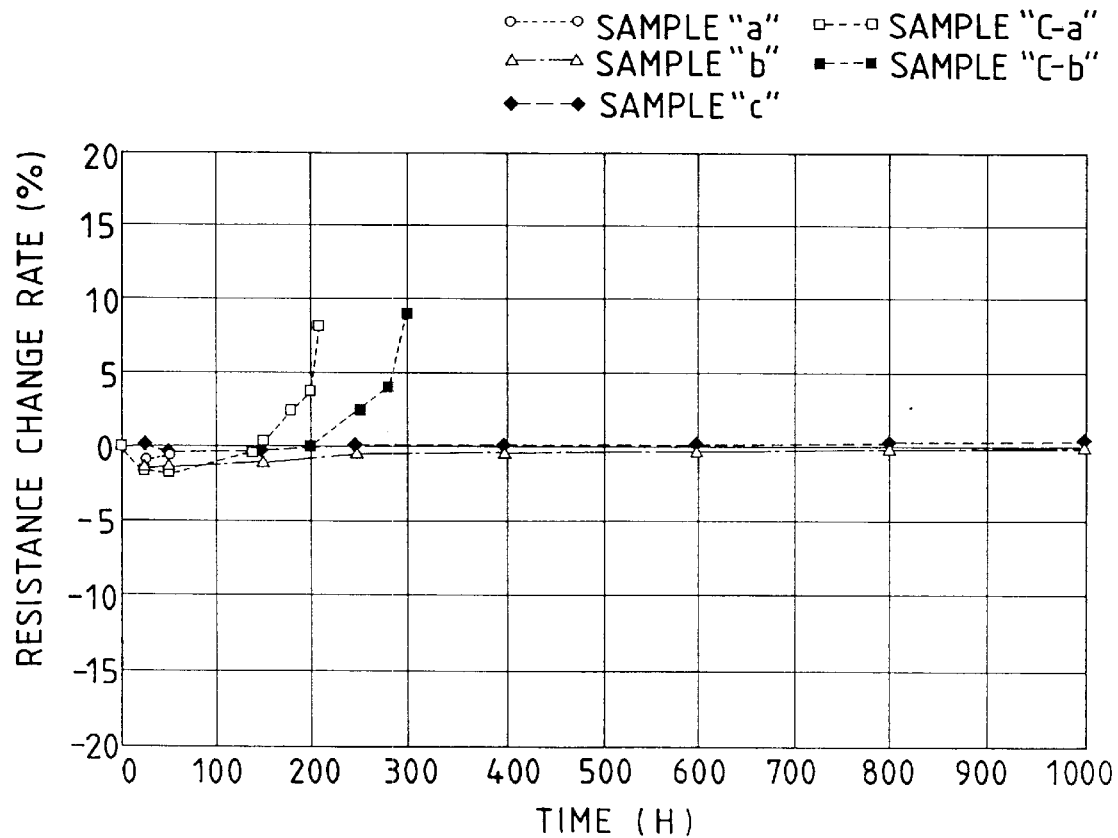
FIG. 16 is a graph showing the effect of the flush surface formed in accordance with the sixth embodiment of the present invention.

FIG. 16 shows a measurement result of experiments conducted to check a relationship between a current supplied to the heater layer and the durability of the same, under a temperature of 900° C. In these experiments, a change rate of the resistance between heater terminals is measured at the room temperature (20° C.±1° C.) by a digital multimeter.

According to FIG. 16, samples a–c did not cause a substantial change of resistance after a time elapse of 1,000 hours. This means that these samples, as oxygen concentration sensing element, have excellent durabilities.

On the other hand, samples C-a and C-b have caused large changes of resistance values even after a time elapse of 50–200 hours. This means that samples C-a and C-b have poor durabilities.

From the result of these experiments, it is concluded that providing a flush surface on the first insulating layer and foig a heater layer on this flush surface is effective to obtain an oxygen concentration sensing element having an excellent durability.

As apparent from the foregoing description, the sixth embodiment of the present invention provides a flush surface partly formed on the first insulating layer, and the heater layer is formed on the flush surface.

In general, the first insulating layer is formed by a plasma spray. Thus, the surface of the first insulating layer is finished unevenly. When the heater layer is provided on such an uneven surface of the first insulating layer, there is a tendency that the thickness of the heater layer is unevenly dispersed. A thin portion, i.e., a high-resistance region, of the heater layer will generate a great amount of heat. Hence, the temperature of the heater layer is locally increased at thin portions which may be deteriorated early.

Furthermore, the uneven surface of the first insulating layer may allow bubbles to enter between the heater layer and the first insulating layer. Due to the presence of these bubbles, the heater layer may floated or peel off the first insulating layer after the heater layer is baked to the first insulating layer. Furthermore, heat of the heater layer is accumulated in the floated or peeled region, rather than transmitted smoothly to the solid electrolyte. Accordingly, the floated or peeled region is subjected to extraordinary high temperatures, and will deteriorate early. This is the reason why the flush surface is provided on the surface of the first insulating layer.

Providing the flush surface on the surface of the first insulating layer makes it possible to provide a heater layer having a uniform thickness and an excellent airtightness. Hence, the durability of the heater layer is improved. A grinding stone can be used for forming the flush surface on the surface of the first insulating layer. Alternatively, an appropriate cutting tool can be used for forming the flush surface.

When the flush surface is formed, there is a possibility of causing a stepped portion. If such a stepped portion is formed, electric parts including the heater layer and the heater lead may be broken. To eliminate this kind of problem, it is preferable to provide a tapered portion connecting the flush surface and the uneven surface, as shown in FIGS. 15A–15D.

From the experiments conducted to assure optimum properties to the flush surface, it is concluded that the flush surface has a surface roughness of 0–30 μm as a mean value of ten measurement points (JIS B0601-1982).

With provision of the flush surface having a surface roughness defined above, it becomes possible to a durable heater layer having a uniform thickness and an excellent airtightness to the first insulating layer.

When the surface roughness of the flush surface exceeds 30 μm, there is a possibility of deteriorating the durability of the heater layer.

Seventh embodiment

A seventh embodiment of the present invention provides an oxygen concentration sensing element having a first insulating layer on which a flush surface is partly formed a heater layer is formed on this flush surface.

Figure 17:
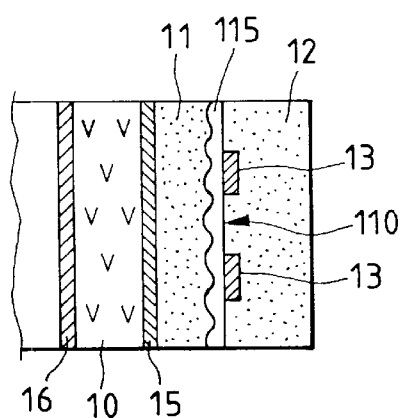
FIG. 17 is a cross-sectional view showing an essential arrangement of an oxygen concentration sensing element in accordance with a seventh embodiment of the present invention.

As shown in FIG. 17, the flush surface 110 of the oxygen concentration sensing element of the seventh embodiment is constituted by a surface layer 115 provided on the first insulating layer 11.

A manufacturing method of this oxygen concentration sensing element will be explained hereinafter.

First, in the same manner as in the first embodiment, external electrode 15, internal electrode 16 and first insulating layer 11 are formed on the wall surfaces of solid electrolyte 10. Then, flush surface 110 is formed on the outer surface of the first insulating layer 11.

For forming the flush surface 110, paste or slurry containing heat-resistive metallic oxide powder used for forming the first insulating layer 11, is prepared. This paste or slurry is applied on a predetermined region of first insulating layer 11 by a spraying or dipping. Then, the paste or slurry is baked to form the surface layer 115.

Subsequently, in the same manner as in the first embodiment, heater layer 13 is provided and second insulating layer 12 is provided outside the heater layer 13, thereby obtaining an oxygen concentration sensing element. Other arrangements are substantially similar to those disclosed in the first embodiment.

According to the seventh embodiment, it becomes possible to obtain an oxygen concentration sensing element having an excellent durability in the same manner as in the sixth embodiment. Functions and effects similar to those of the first embodiment can be obtained.

Eighth embodiment

An eighth embodiment of the present invention provides an oxygen concentration sensing element having a heater layer made of platinum and gold.

The oxygen concentration sensing element of the eighth embodiment, in the same manner as the first embodiment explained previously with reference to FIGS. 1A through 3, comprises cup-shaped solid electrolyte 10, external electrode 15 provided on the outer wall surface of solid electrolyte 10, and internal electrode 16 provided on the inner wall surface of solid electrolyte 10. First insulating layer 11, formed by a gas-permeable and electrically nonconductive porous material, is provided on the surface of the external electrode 15 at least in a region used for the detection of oxygen concentration. Second insulating layer 12, which is electrically nonconductive, is provided outside the first insulating layer 11. Heater layer 13 is provided between the first insulating layer 11 and the second insulating layer 12.

The heater layer 13 is made of an alloy of platinum and gold. It is allowed that this alloy contains, as additives, hyaline of 0.5–20 weight % and metallic oxide (e.g., heat-resistive insulating oxide such as $Al_2O_3$ and conductive oxide material such as $LaSrMnO_3$ or $LaSrCrO_3$) of 0.5–20 weight %.

Adding the hyaline is effective to enhance airtightness of heater layer 13 to the insulating layer 11. Adding the metallic oxide is effective to enhance the heat-durability of heater layer 13. Other arrangements are substantially similar to those of the first embodiment.

Next, a relationship between the material of the heater layer and the response of the oxygen concentration sensing element will be explained with reference to Table 2.

In Table 2, each sample is an oxygen concentration sensing element having a heater layer 13 made of an alloy containing platinum and gold. A weight ratio of platinum and gold is different in each sample. Samples 2-5 has no heater layer between first insulating layer 11 and second insulating layer 12. The response of each sample is measured in the same manner as in the first embodiment.

As shown in Table 2, samples 2-3 and 2-4 have excellent response comparable with sample 2-5. However, samples 2-1 and 2-2 are inferior in their responses.

From the foregoing, it is concluded that forming the heater layer by an alloy of platinum and gold with a predetermined mixing ratio is advantageous to obtain an oxygen concentration sensing element having an excellent response.

TABLE 2

| Sample No. | Weight Ratio of Au/Pt in Heater layer | Response |
|---|---|---|
| 2-1 | 0/100 | X |
| 2-2 | 0.2/99.9 | X |
| 2-3 | 0.5/99.5 | ○ |
| 2-4 | 2/98 | ○ |
| 2-5 | — | ○ |

Ninth embodiment

A ninth embodiment of the present invention provides an oxygen concentration sensing element having a heater layer of a multilayer construction.

Figure 18:
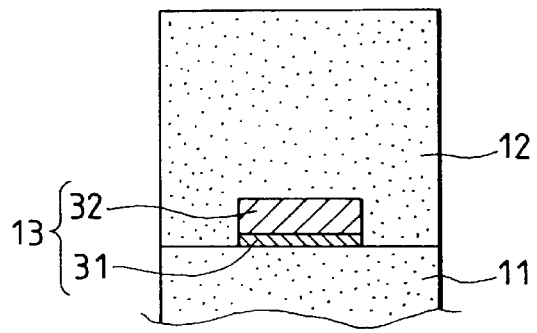
FIG. 18 is a cross-sectional view showing a two-layer structure of a heater layer in accordance with a ninth embodiment of the present invention.

As shown in FIG. 18, the oxygen concentration sensing element of the ninth embodiment comprises, as well as the cup-shaped solid electrolyte with internal and external electrodes formed on its inner and outer wall surfaces, first insulating layer 11 formed on the external electrode at least in a region used for the detection of oxygen concentration. Second insulating layer 12 is provided outside the first insulating layer 11. Heater layer 13 is provided between first insulating layer 11 and second insulating layer 12.

Heater layer 13 comprises a first heater layer 31 and a second heater layer 32. First heater layer 31 has a thickness of approximately 8 μm and is provided directly on the first insulating layer 11. Second heater layer 32 has a thickness of approximately 10–60 μm and is accumulated on the first heater layer 31.

These first heater layer 31 and second heater layer 32 are made of an alloy chiefly containing platinum and gold. The first heater layer 31 comprises hyaline of 10 weight %, as an additive. The second heater layer 32 comprises hyaline of 5 weight %, as an additive. Other arrangements are substantially similar to those of the first embodiment.

According to the oxygen concentration sensing element of the ninth embodiment, the first heater layer 31 is directly brought into contact with the first insulating layer 11 and contains hyaline whose weight ratio is relatively large. On the other hand, the second heater layer 32 is spaced from the first insulating layer 11 and contains hyaline whose weight ratio is relatively small.

Adding hyaline is chiefly for enhancing the airtightness of heater layer 13 to first insulating layer 11. However, hyaline itself is not an electrically conductive material. Hence, the presence of hyaline may reduce the heating efficiency of heater layer 13.

In view of the above, the first heater layer 31 contains a relatively large amount of hyaline provide a satisfactory airtightness. On the other hand, the second heater layer 32 contains a relatively small amount of hyaline the second heater layer 32 is not required to possess a highly airtightness, rather for increasing the heating efficiency. Thus, the ninth embodiment makes it possible to realize an oxygen concentration sensing element satisfy all the requirements of heating efficiency and airtightness to the first insulating layer. Other arrangements are substantially similar to those disclosed in the first embodiment.

Figure 19:
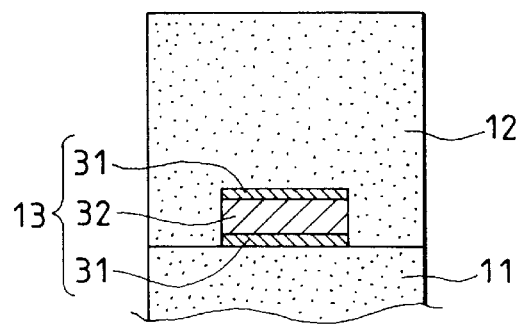
FIG. 19 is a cross-sectional view showing a three-layer structure of a heater layer in accordance with the ninth embodiment of the present invention.

FIG. 19 shows a modification of the ninth embodiment, according to which another first heater layer 31 is accumulated on the second heater layer 32 to constitute a three-layer construction.

Figure 20:
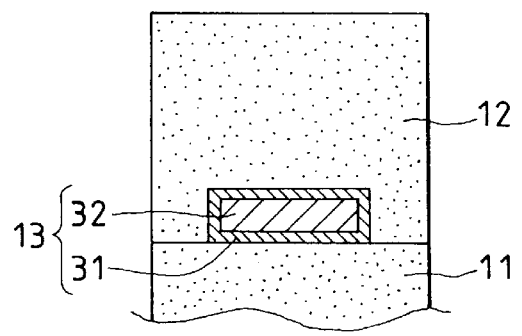
FIG. 20 is a cross-sectional view showing another arrangement of the heater layer in accordance with the ninth embodiment of the present invention.

FIG. 20 shows another modification of the ninth embodiment, according to which first heater layer 31 is provided entirely around the second heater layer 32 to enclose the second heater layer 32.

Both of the above-described modified examples can obtain the functions and effects similar to those of the oxygen concentration sensing element shown in FIG. 18. The multilayer construction disclosed in the ninth embodiment can also be applied to the heater lead portion.

Tenth embodiment

A tenth embodiment of the present invention provides an oxygen concentration sensing element having a heater lead portion made of gold.

The oxygen concentration sensing element of the tenth embodiment, in the same manner as the first embodiment explained previously with reference to FIGS. 1A through 3, comprises cup-shaped solid electrolyte 10, external electrode 15 provided on the outer wall surface of solid electrolyte 10, and internal electrode 16 provided on the inner wall surface of solid electrolyte 10. First insulating layer 11, formed by a gas-permeable and electrically nonconductive porous material, is provided on the surface of the external electrode 15 at least in a region used for the detection of oxygen concentration. Second insulating layer 12, which is electrically nonconductive, is provided outside the first insulating layer 11. Heater layer 13 is provided between the first insulating layer 11 and the second insulating layer 12.

Heater layer 13 is provided in the region of closed end portion 101 of the solid electrolyte 10. Heater terminals 131 and 132 are provided on the barrel portion 102 of solid electrolyte 10. These heater terminals 131 and 132 are connected via heater lead 130 to the heater layer 13. The heater layer 13 is made of an alloy of platinum and gold. The heater lead 130 and heater terminals 131 and 132 are made of gold.

The heater lead 130 can contain, as additives, hyaline of 0.5–20 weight % and metallic oxide (e.g., heat-resistive insulating oxide such as $Al_2O_3$ and conductive oxide material such as $LaSrMnO_3$ or $LaSrCr_3$) of 0.5–20 weight %.

Adding the hyaline is effective to enhance airtightness of heater layer 13 to the insulating layer 11. Adding the metallic oxide is effective to enhance the heat-durability of heater layer 13. Other arrangements are substantially similar to those of the first embodiment.

According to the oxygen concentration sensing element of the tenth embodiment, the heater lead 130 is made of gold.

This is effective to suppress the catalytic action in the heater lead 130. Accordingly, it becomes possible to prevent heater lead 130 from being deteriorated or broken due to deposition of carbon in the heater lead 130.

Furthermore, according to the oxygen concentration sensing element of the tenth embodiment, heater lead 130 is made of gold and the heater layer 13 is made of an alloy of platinum and gold. Therefore, heat generation is concentrated in the heater layer 13 because heater layer 13 has a higher electric resistance. Electric power supplied to heater layer 13 and heater lead 130 can be consumed effectively for heating the external electrode 15. Other arrangements are substantially the same as those disclosed in the first embodiment.

Eleventh embodiment

An eleventh embodiment of the present invention provides modifications of the heater layers, heater leads and heater terminals.

As shown in the development view of FIGS. 21 through 27, the oxygen concentration sensing element can have various heater layers 13 and associated heater leads 130 and heater terminals 131 and 132.

Figure 21:
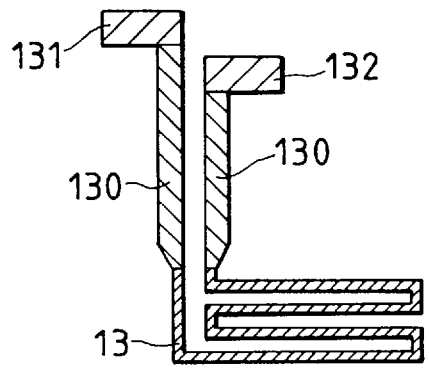
FIGS. 21 through 27 are development views showing various heaters in accordance with an eleventh embodiment of the present invention.
Figure 22:
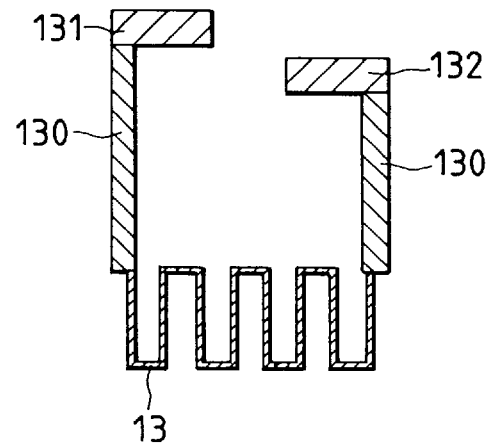
Figure 23:
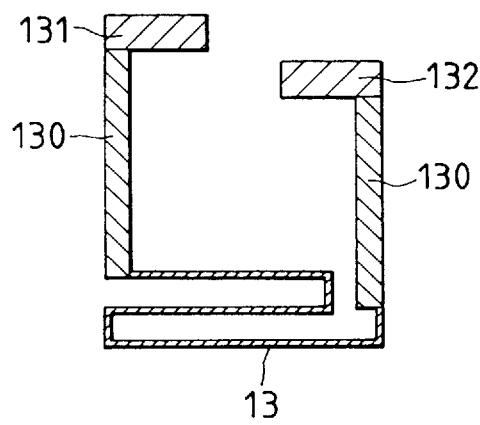

According to the examples disclosed in FIGS. 21 to 23, heater layer 13 has a relatively thin width and is arranged into a comb-teeth pattern.

Figure 24:
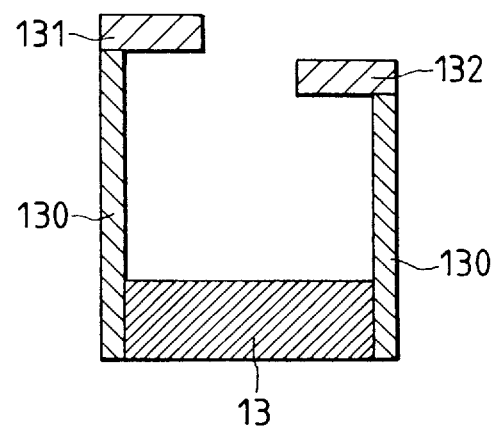
Figure 25:
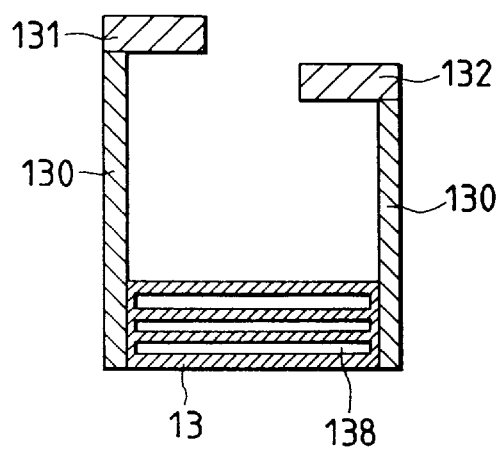
Figure 26:
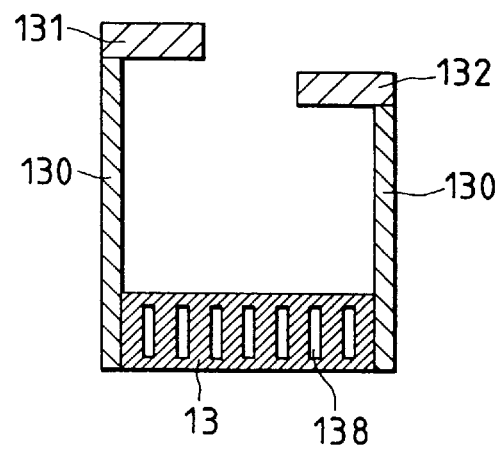
Figure 27:
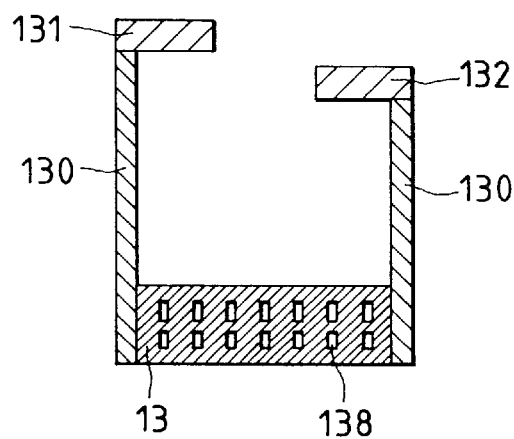

A heater layer 13 disclosed in FIG. 24 is a plan heater layer having a relatively wide area. Examples disclosed in FIGS. 25–27, a plurality of slits are provided on the plane heater layer disclosed in FIG. 24. Other arrangements are substantially the similar to those disclosed in the first embodiment.

Functions and effects of the eleventh embodiment will be explained hereinafter.

As shown in FIGS. 21–23, when the heater layer 13 is formed into a comb-teeth pattern, the measured gas can be introduced through clearances of heater layer 13. Hence, the measured gas can be smoothly introduced from the second insulating layer via the heater layer to the external electrode, and can be smoothly discharged in the opposite direction. In other words, an air-fuel ratio sensing element having an excellent response can be obtained.

The heater layer 13 disclosed in FIG. 24 is advantageous in the external electrode can be heated uniformly. This is effective to reduce the internal stress in the insulating layers. Thus, it becomes possible to prevent insulating layers from being cracked. Thus, the reliability of the air-fuel ratio sensing element can be improved.

The heater layers 13 disclosed in FIGS, 25–27 make it possible to smoothly introduce the measured gas through slits 138. Furthermore, the functions and effects similar to those of the first embodiment can be obtained.

Twelfth embodiment

A twelfth embodiment of the present invention will be explained with reference to FIGS. 28A through 33. An oxygen concentration sensing element of the twelfth embodiment is a limiting-current type air-fuel ratio sensing element.

As shown in FIGS. 28A and 28B, the oxygen concentration sensing element 1 comprises a cup-shaped solid electrolyte 10 with one end (i.e., its top) opened and the other end (i.e., its bottom) closed, an external electrode 15 provided on an outer wall surface of this solid electrolyte 10 and exposed to measured gas, and an internal electrode 16 provided on an inner wall surface of the solid electrolyte 10 in a confronting relationship with the external electrode 15 via the solid electrolyte 10.

Figure 29:
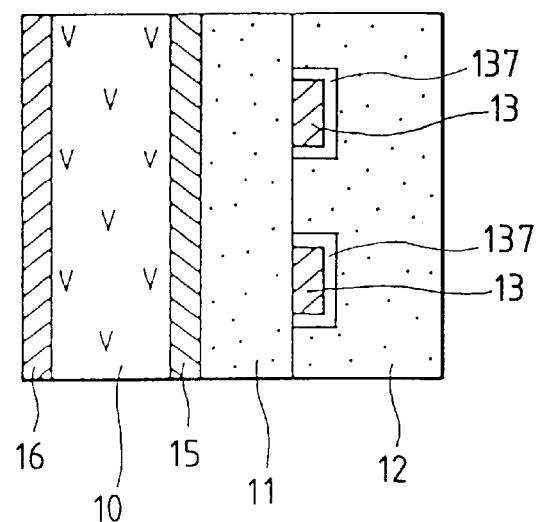
FIG. 29 is a vertical cross-sectional view showing an essential arrangement of the oxygen concentration sensing element in accordance with the twelfth embodiment of the present invention.

As shown in FIG. 29, a first insulating layer 11, formed by a gas-permeable and non-conductive porous material, is provided on the surface of external electrode 15 at least a region used for detection of oxygen concentration. An electrically nonconductive insulating layer 12 is provided outside the first insulating layer 1 1. A heater layer 13 is interposed between first insulating layer 11 and second insulating layer 12.

The entire surface of heater layer 13 is covered by a gas protecting layer 137 having a gas permeability lower than that of the first insulating layer 11. The gas protecting layer 137 has a thickness of 20 $\mu$m and a porous rate equal to or smaller than 1%, and is made of borosilicate glass.

The solid electrolyte 10, as shown in FIGS. 28A and 28B, comprises a closed end portion 101 around which external electrode 15 is wound cylindrically, and a barrel portion 102 having a diameter larger than that of closed end portion 101. A flange portion 19 is provided on a cylindrical outer surface of barrel portion 102 so as to protrude radially outward therefrom at the center thereof.

Solid electrolyte 10 is provided with an external electrode lead 150 and an external electrode terminal 151 which are extended from external electrode 15.

Figure 30:
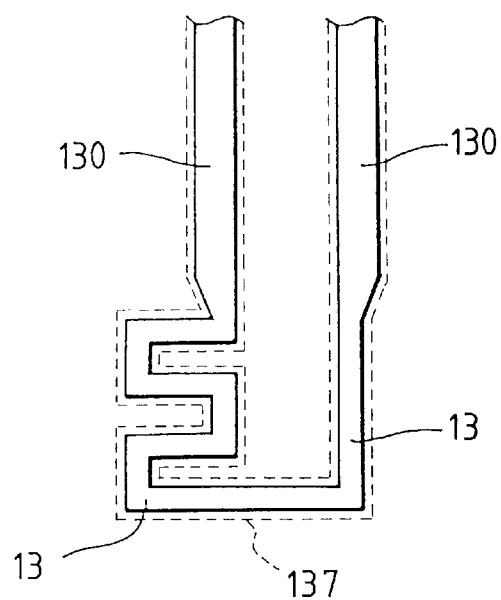
FIG. 30 is a development view showing a heater layer and a gas protecting layer incorporated in the oxygen concentration sensing element in accordance with the twelfth embodiment of the present invention.

Heater layer 13, as shown in FIG. 30, is provided on the external electrode 15 via first insulating layer 11. There are heater terminals 131 and 132 provided on the surface of barrel portion 102 of solid electrolyte 10, each of heater terminals 131 and 132 extending along the outer wall surface of solid electrolyte 10 and being connected to heater layer 13 via a heater lead 130.

As shown in FIGS. 28A, 28B and 29, gas protecting layer 137 covers the entire surface of the heater lead 130 as well as heater layer 13.

As shown in FIGS. 28A, 28B and 30, each of heater lead 130, heater terminals 131 and 132 has a width thicker than that of heater layer 13. Furthermore, heater terminals 131 and 132 are connected to both ends of a single elongated heater layer 13. A positive voltage is applied through one heater terminal 131 is applied a positive voltage, while a negative voltage is applied to the other heater terminal 132.

First and second insulating layers 11 and 12 are provided below the flange portion 19 of solid electrolyte 10.

The oxygen concentration detector 2 incorporating the oxygen concentration sensing element 1 of the twelfth embodiment has the same arrangement of the first embodiment shown in FIG. 4.

Next, a manufacturing method of the above-described oxygen concentration sensing element 1 will be explained.

First of all, starting material, such as $ZrO_2$, is pressurized and molded into a cup-shaped configuration. Then, the molded material as baked at a temperature of 1,400° C. to 1,600° C., to obtain the cup-shaped solid electrolyte 10.

Internal electrode 16, external electrode 15, the electrode leads, and the electrode terminals are formed on the inner and outer wall surfaces of solid electrolyte 10 by a sputtering or plating noble metallic powder, such as Pt.

Subsequently, first insulating layer 11 is formed by plasma spraying heat-resistive metallic oxide powder, such as magnesia-alumina spinel, on the outer wall surface of solid electrolyte 10 at a predetermined region below flange portion 19 and the surface of external electrode 15.

Next, paste "a" containing platinum for forming the heater layer 13 or the like is prepared. At the same time, paste "b" containing borosilicate glass for forming the gas protecting layer 137 is prepared.

First, paste "b" is applied on the wall surface of solid electrolyte 10 in a pattern shown in the development view of FIG. 30. Then, paste "a" is accumulated on the surface of paste "b". Furthermore, the paste "b" is accumulated on the surface of the paste "a" so as to form the structure shown in FIG. 29.

After that, by thermally processing these pastes at a temperature of 900° C. to 1,100° C., heater layer 13, heater lead 130, heater terminal 131 and gas protecting layer 137 are formed.

Next, second insulating layer 12 is formed by plasma spraying the above heat-resistive metallic oxide powder on the gas protecting layer 137 and the first insulating layer 11. Through the above processing, the oxygen concentration sensing element 1 of the twelfth embodiment is obtained.

Next, the characteristics of oxygen concentration sensing element 1 of the twelfth embodiment of the present invention will be explained with reference to the evaluation result shown in Table 3.

In Table 3, samples 3-1 through 3-4 and 3-7 are oxygen concentration sensing elements manufactured in accordance with the twelfth embodiment of the present invention, but are different in the thicknesses and porous rate of the gas protecting layer 137. Sample 3-5 is an oxygen concentration sensing element similar to the above samples 3-1 through 3-4 and 3-7 but different in that no gas protecting layer is provided around the heater layer 13. Samples 3-6 and 3-8 are comparative examples. On the other hand, sample 3-9 is oxygen concentration sensing element 9 shown in FIGS. 34 and 35 which comprises solid electrolyte 90, external electrode 95 provided on the outer wall surface of solid electrolyte 90, internal electrode 96 provided on the inner wall surface of solid electrolyte 90, and insulating layer 91 provided on the surface of external electrode 95. The oxygen concentration sensing element 9 comprises inside chamber 92 for introducing referential gas. Round stick-like heater 99 is inserted into this inside chamber 92 and settled there. The heater 99 is formed by silicon nitride with a heater element involved therein.

The performance evaluation is conducted on each of "R(rich)-L(lean) response", "L(lean)-R(rich) response" and "output current".

In the evaluation on the "R-L response" and "L-R response", samples 3-1 to 3-8 are incorporated in the oxygen concentration detector (FIG. 4) which is installed on the exhaust system of a 2,000 cc, 6-cylinder engine. A fuel injection amount of an injector of this engine is varied widely, at an engine speed of 1,100 rpm/s, so as to switch the air-fuel ratio from 14 to 15 (for the test of "R-L response) and from 15 to 14 (for the test of "L-R response) to measure a response time of the oxygen concentration detector. A sample having a response time equal to or smaller than 200 ms is denoted by "O", while a sample having a response time larger than 200 ms is denoted by "X" in Table 3.

When an output current value of the above-described (limiting-current type) oxygen concentration causes a change of a width of 100 in response to the switching of the air-fuel ratio, the response time is defined as a time required to reach a 63% point of the entire change width from the moment the air-fuel ratio is switched.

Furthermore, the output current of each oxygen concentration sensing element is measured when the air-fuel ratio is 15. A sample having an output current in a range of 6–8 mA is denoted by "0", while other samples are denoted by "X" in Table 3.

From the result of Table 3, samples 3-1 through 3-4 and 3-7 have adequate performances in all of the "R-L response", "L-R response" and "output current", and therefore their excellent performances as an oxygen concentration sensing element are proved. Sample 3-6 has a poor "output current" due to its large thickness. This is disadvantageous in that the sensing accuracy is lowered. Sample 3-8 has a poor "R-L and L-R response" due to its thin thickness and large porous rate of the gas protecting layer.

Sample 3-9, although having a satisfactory performance, is inferior in its warm-up ability as described previously.

Regarding the relationship between the limiting current and the air-fuel ratio, there is no substantial difference between the twelfth embodiment and the conventional art in the same manner as the first invention shown in FIG. 6.

Figure 31:
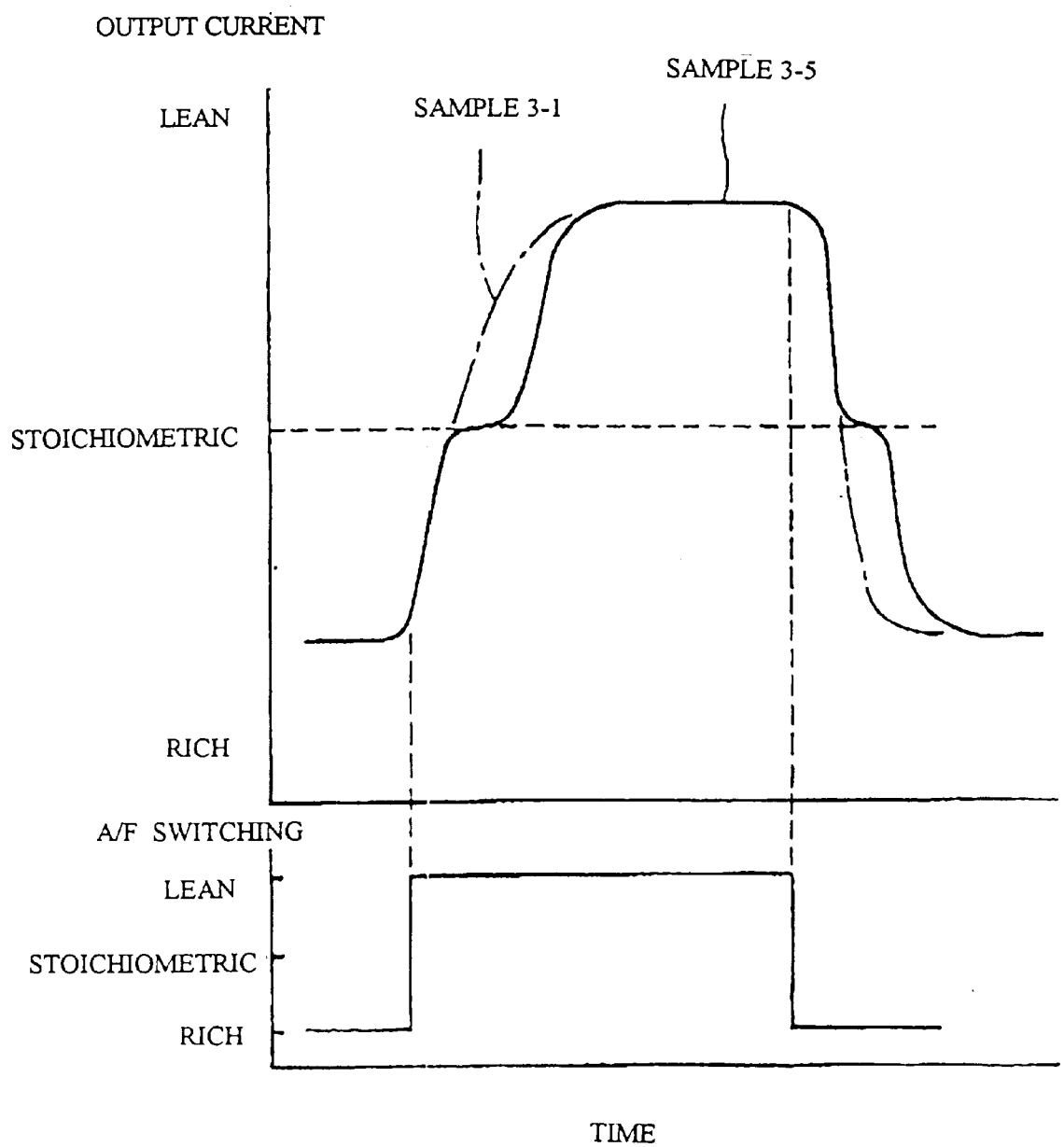
FIG. 31 is a graph showing a relationship between an output current and an air-fuel ratio of the oxygen concentration sensing element of the twelfth embodiment of the present invention.
Figure 34:
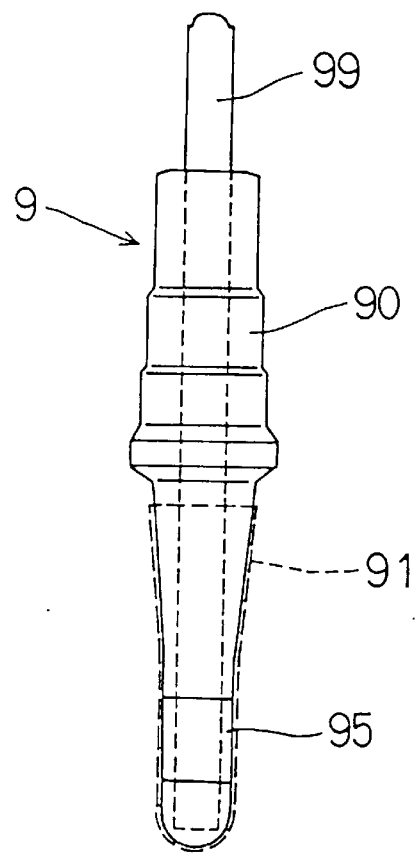
Figure 35:
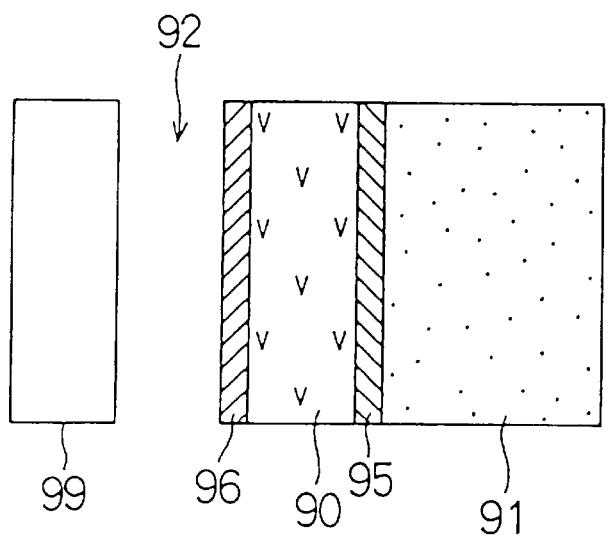

FIG. 31 shows output waveforms of oxygen concentration sensing element 1 (sample 3-1) of the twelfth embodiment and the oxygen concentration sensing element (sample 3-5) having no gas protecting layer 137 in relation to a switching timing of the air-fuel ratio.

According to the result of FIG. 31, the oxygen concentration sensing element of the twelfth embodiment is excellent in the response characteristics crossing the stoichiometric point, due to the provision of the gas protecting layer covering the heater layer.

TABLE 3

| Sample No. | Gas protecting layer Thickness | Porous rate | R-L response | | L-R response | | Output current |
|---|---|---|---|---|---|---|---|
| 3-1 | 20 μm | 1% or less | 120 ms | O | 130 ms | O | O |
| 3-2 | 50 μm | 1% or less | 130 ms | O | 140 ms | O | O |
| 3-3 | 100 μm | 1% or less | 150 ms | O | 170 ms | O | O |
| 3-4 | 20 μm | 4% | 160 ms | O | 180 ms | O | O |
| 3-5 | — | | 350 ms | X | 370 ms | X | O |
| 3-6 | 200 μm | 1% or less | 160 ms | O | 180 ms | O | X |
| 3-7 | 20 μm | 5% | 180 ms | O | 200 ms | O | O |
| 3-8 | 20 μm | 7% | 340 ms | X | 360 ms | X | O |
| 3-9 | — | | 100 ms | O | 105 ms | O | O |

Next, functions and effects of the twelfth embodiment will be explained. According to the twelfth embodiment, heater layer 13 is provided between first insulating layer 11 and second insulating layer 12. The entire surface of heater layer 13 is covered by gas protecting layer 137. This arrangement is effective to prevent the measure gas from directly contacting the heater layer 13. Accordingly, oxygen contained in the measure gas can surely reach the external electrode 15 without being absorbed by the heater layer 13. Accordingly, the variation of oxygen concentration in the measured gas can be quickly sensed by the oxygen concentration sensing element 1.

Furthermore, the distance between heater layer 13 and solid electrolyte 10 is in a level of hundreds μm. Therefore, most of heat generated from the heater layer 13 is quickly transmitted to the external electrode 15. Hence, oxygen concentration sensing element 1 has an excellent warm-up ability.

Moreover, heater layer 13 is not exposed on the outer surface of oxygen concentration sensing element 1, and covered by the second insulating layer 12. Thus, it becomes possible to suppress the loss of thermal energy generated from heater layer 13.

As explained above, the twelfth embodiment of the present invention provides an air-fuel ratio sensing element having an excellent warm-up ability and a reliable response.

The gas protecting layer of the twelfth embodiment can also be applied to an oxygen concentration cell type sensing element (refer to FIG. 7). Similar factions and effects will be obtained.

Figure 32A:
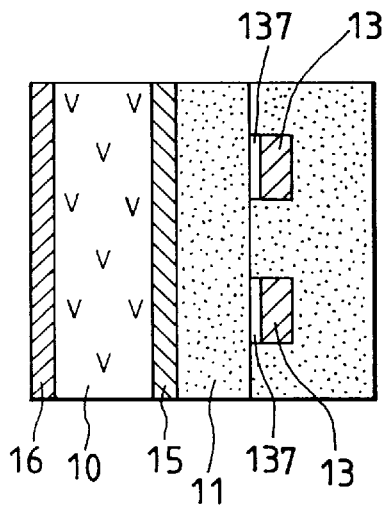
FIGS. 32A and 32B are vertical cross-sectional view showing essential arrangements of modified twelfth embodiment of the present invention.
Figure 32B:
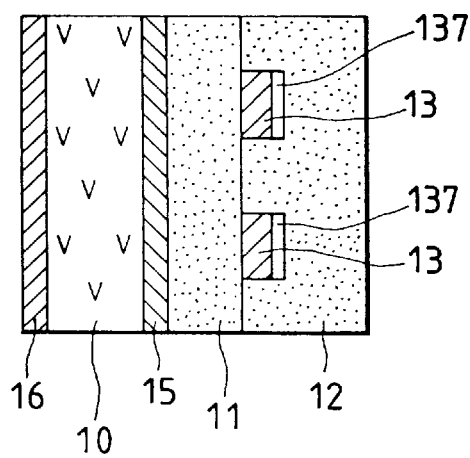
Figure 33:
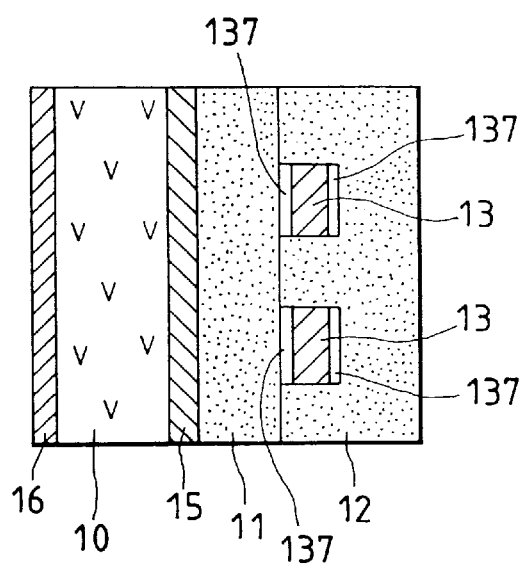
FIG. 33 is a vertical cross-sectional view showing an essential arrangement of another modified twelfth embodiment of the present invention.

FIGS. 32A and 32B show modifications of the twelfth embodiment. According to the example of FIG. 32A, the gas protecting layer 137 is provided on only one surface bounding to the first insulating layer 11. According to the example of FIG. 32B, the gas protecting layer 137 is provided on another surface bounding to the second insulating layer 12. FIG. 33 shows another example which is substantially the combination of the examples shown in FIGS. 32A and 32B.

Furthermore, it is preferable that the gas protecting layer is made of a heat-resistive inorganic oxide having a porous rate not larger than 5%. This is advantageous to surely prevent he measured gas from contacting the heater layer, and to obtain a gas protecting layer having an excellent durability.

If the porous rate exceeds 5%, there is a possibility that the function of gas protecting may not be surely effected. Hence, it is preferable to set the porous rate as small as possible.

Moreover, it is preferable that the heat-resistive inorganic oxide is glass, such as borosilicate glass and flint glass, or ceramic, such as $Al_2O_3$, $Al_2O_3$—$Si_2$. These materials can protect the platinum of heater layer from the measured gas.

When glass is selected as the heat-resistive inorganic oxide, it is preferable to add bivalent element having a large ionic radius, such as Ba, Pb, Sr, Ca, Cd. This is effective to prevent the electric conductivity of the gas protecting layer (i.e, heater coating layer).

When glass is selected as the heat-resistive inorganic oxide, it is preferable to use crystallized glass because the heat durability of the heater layer can be enhanced.

Still further, it is preferable that the gas protecting layer has a thickness of 1–100 $\mu$m. With this size, it becomes possible to satisfy both of the requirements of preventing the measured gas from contacting the heater layer and obtaining an adequate diffusibility of the measured gas in the insulating layers.

When the thickness is less than 1 $\mu$m, it is difficult to provide a uniform layer. It may result in a failure in protecting the measured gas form contacting the heater layer. On the other hand, when the thickness is larger than 100 $\mu$m, the diffusibility of the measured gas is worsened and therefore the output current of the oxygen concentration sensing element may be attenuated.

As this invention may be embodied in several forms without departing from the spirit of essential characteristics thereof, the present embodiments as described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensing element comprising:
a solid electrolyte formed into a cup-shaped configuration with one end opened and the other end closed;
an external electrode provided on an outer wall surface of said solid electrolyte so as to be exposed to measured gas, said external electrode having a lateral surface area;
an internal electrode provided on an inner wall surface of said solid electrolyte in a confronting relationship to said external electrode
a first insulating layer provided on said external electrode at least in a region used for detection of an air-fuel ratio, said first insulating layer being formed by a gas-permeable and nonconductive porous material and having a thickness of 10–900 $\mu$m and a porous rate of 1–50%;
a second insulating layer provided outside said first insulating layer, said second insulating layer being nonconductive; and
a heater layer provided between said first insulating layer and said second insulating layer, said heater layer having a lateral surface area which overlaps the lateral surface area of the external electrode and is separated at least in part from the lateral surface area of the external electrode by said first insulating layer.

2. The air-fuel ratio sensing element in accordance with claim 1, wherein said second insulating layer is formed by a gas-permeable porous material.

3. The air-fuel ratio sensing element in accordance with claim 1, wherein said second insulating layer is formed by a gas impervious material.

4. The air-fuel ratio sensing element in accordance with claim 1, wherein said heater layer is formed by a conductive material and hyaline.

5. The air-fuel ratio sensing element in accordance with claim 1, wherein said heater layer is formed by a conductive material, and said conductive material contains at least one of noble metallic powder and perovskite type oxide powder.

6. The air-fuel ratio sensing element in accordance with claim 1, wherein said heater layer is made of metallic wire or metallic foil.

7. The air-fuel ratio sensing element in accordance with claim 1, further comprising a heater lead connected to said heater layer, an external electrode lead connected to said external electrode, and an internal electrode lead connected to said internal electrode, wherein said heater lead, said external electrode and said internal electrode are provided along the wall surfaces of said solid electrolyte.

8. The air-fuel ratio sensing element in accordance with claim 7, wherein said heater lead and said external electrode lead have a catalytic action of oxidation and reduction to said measured gas smaller than that of said external electrode.

9. The air-fuel ratio sensing element in accordance with claim 8, wherein said heater lead is made of gold.

10. The air-fuel ratio sensing element in accordance with clam 8, wherein said heater lead is made of an alloy containing gold and at least one other component selected from the group consisting of Pt, Pd, Rh and Ir.

11. The air-fuel ratio sensing element in accordance with claim 1, wherein said solid electrolyte has a closed end portion closer to said other end and a barrel portion formed at an intermediate portion, and said heater is provided in a predetermined region of said closed end portion while a heater terminal is provided on said barrel portion, and said heater terminal is connected to said heater layer via a heater lead.

12. The air-fuel ratio sensing element in accordance with claim 11, wherein said first insulating layer is formed on the outer wall surface of said solid electrolyte so as to extend to a region of said heater terminal.

13. The air-fuel ratio sensing element in accordance with claim 1, wherein a flush surface is partly formed on said Erst insulating layer, and said heater layer is formed on said flush surface.

14. The air-fuel ratio sensing element in accordance with claim 13, wherein said flush surface has a surface roughness of 0–30 $\mu$m.

15. The air-fuel ratio sensing element in accordance with claim 1, wherein said heater layer has an oxygen absorbing force weaker than that of said external electrode.

16. The air-fuel ratio sensing element in accordance with claim 15, wherein said heater layer is made of an alloy comprising platinum and gold, with a mixing rate of said gold being in a range of 0.5–50 weight %.

17. The air-fuel ratio sensing element in accordance with claim 15, wherein said heater layer contains platinum and at least one other component selected from the group consisting of Pd, Rh and Ir.

18. The air-fuel ratio sensing element in accordance with claim 1, wherein the lateral surface area of said heater layer overlaps 10–80% of the lateral surface area of said external electrode.

19. An air-fuel ratio detector comprising an air-fuel ratio sensing element and a housing accommodating said air-fuel ratio sensing element, wherein said air-fuel ratio sensing element comprises:
a solid electrolyte formed into cup-shaped configuration with one end opened and the other end closed;
an external electrode provided on an outer wall surface of said solid electrolyte so as to be exposed to measured gas, said external electrode having a lateral surface area;
an internal electrode provided on an inner wall surface of said solid electrolyte in a confronting relationship to said external electrode;
a first insulating layer provided on said external electrode at least in a region used for detection of an air-fuel ratio, said first insulating layer being formed by a gas-permeable and nonconductive porous material and having a thickness of 10–900 μm and a porous rate of 1–50%;
a second insulating layer provided outside said first insulating layer, said second insulating layer being nonconductive; and
a heater layer provided between said first insulating layer and said second insulating layer, said heater layer having a lateral surface area which overlaps the lateral surface area of the external electrode and is separated at least in part from the lateral surface area of the external electrode by said first insulating layer.

20. The air-fuel ratio detector in accordance with claim 19, wherein said air-fuel ratio sensing element is directly supported by said housing.

21. The air-fuel ratio detector in accordance with claim 19, wherein said air-fuel ratio sensing element is indirectly supported by said housing via a metallic washer.

22. The air-fuel ratio detector in accordance with claim 19, wherein said air-fuel ratio sensing element is indirectly supported by said housing via an insulator.

23. The air-fuel ratio detector in accordance with claim 19, wherein said second insulating layer is formed along the outer surface of said first insulating layer so as to extend to a region where said air-fuel ratio sensing element is supported to said housing.

24. The air-fuel ratio detector in accordance with claim 19, wherein the lateral surface area of said heater layer overlaps 10–80% of the lateral surface area of said external electrode.

25. An air-fuel ratio sensing element comprising:
a solid electrolyte formed into a cup-shaped configuration with one end opened and the other end closed;
an external electrode provided on an outer wall surface of said solid electrolyte so as to be exposed to measured gas, said external electrode having a lateral surface area;
an internal electrode provided on an inner wall surface of said solid electrolyte in a confronting relationship to said external electrode;
a first insulating layer provided on said external electrode at least in a region used for detection of an air-fuel ratio, said first insulating layer being formed by a gas-permeable and nonconductive porous material and having a thickness of 10–900 μm and a porous rate of 1–50%;
a second insulating layer provided outside said first insulating layer, said second insulating layer being nonconductive;
a heater layer provided between said first insulating layer and said second insulating layer, said heater layer having a lateral surface area which overlaps the lateral surface area of the external electrode and is separated at least in part from the lateral surface area of the external electrode by said first insulating layer; and a gas protecting layer provided on at least part of a surface of said heater layer, said gas protecting layer having a gas permeability smaller than that of said first insulating layer.

26. The air-fuel ratio sensing element in accordance with claim 25, wherein said gas protecting layer is coated entirely on the surface of said heater layer.

27. The air-fuel ratio sensing element in accordance with claim 25, wherein said gas protecting layer is made of a heat-resistive inorganic oxide having a porous rate not larger than 5%.

28. The air-fuel ratio sensing element in accordance with claim 27, wherein said heat-resistive inorganic oxide is glass or ceramic.

29. The air-fuel ratio sensing element in accordance with claim 25, wherein said gas protecting layer has a thickness of 1–100 μm.

30. The air-fuel ratio sensing element in accordance with claim 25, wherein the lateral surface area of said heater layer overlaps 10–80% of the lateral surface area of said external electrode.

* * * * *